US010314889B2

(12) United States Patent
Wu et al.

(10) Patent No.: US 10,314,889 B2
(45) Date of Patent: *Jun. 11, 2019

(54) SUPPRESSION OF ALLERGIC LUNG INFLAMMATION AND HYPERREACTIVITY

(71) Applicant: The Regents of the University of California, Oakland, CA (US)

(72) Inventors: Reen Wu, Davis, CA (US); Ching-Hsien Chen, Davis, CA (US); Chen-Chen Lee, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,263

(22) PCT Filed: Dec. 19, 2014

(86) PCT No.: PCT/US2014/071658
§ 371 (c)(1),
(2) Date: Jun. 17, 2016

(87) PCT Pub. No.: WO2015/095789
PCT Pub. Date: Jun. 25, 2015

(65) Prior Publication Data
US 2017/0028019 A1    Feb. 2, 2017

Related U.S. Application Data

(60) Provisional application No. 61/919,593, filed on Dec. 20, 2013.

(51) Int. Cl.
| A61K 38/10 | (2006.01) |
| A61K 38/17 | (2006.01) |
| C07K 7/08  | (2006.01) |
| C07K 16/28 | (2006.01) |
| C07K 14/47 | (2006.01) |
| A61K 9/00  | (2006.01) |

(52) U.S. Cl.
CPC .......... A61K 38/177 (2013.01); A61K 9/007 (2013.01); A61K 38/10 (2013.01); A61K 38/1709 (2013.01); C07K 7/08 (2013.01); C07K 14/4703 (2013.01); C07K 16/28 (2013.01)

(58) Field of Classification Search
CPC ...... A61K 38/10; A61K 38/1709; C07K 7/08; C07K 14/47; C07K 14/4702; C07K 14/4703; C07K 14/4705
See application file for complete search history.

(56) References Cited

U.S. PATENT DOCUMENTS

| 2008/0020031 | A1  | 1/2008  | Li et al. |
| 2009/0169559 | A1* | 7/2009  | Cohen-Vered ....... A61K 9/0019 424/141.1 |
| 2009/0203620 | A1  | 8/2009  | Parikh |
| 2009/0220581 | A1  | 9/2009  | Li et al. |
| 2010/0015117 | A1* | 1/2010  | Verma .................... A61K 38/02 424/94.1 |
| 2010/0310568 | A1* | 12/2010 | Prat ....................... A61K 38/08 424/139.1 |
| 2013/0196896 | A1  | 8/2013  | Komatsu et al. |
| 2016/0176936 | A1  | 6/2016  | Wu et al. |

FOREIGN PATENT DOCUMENTS

| WO | WO 2012/006640 A2 * | 1/2012 |
| WO | WO 2015/013669 A1 * | 1/2015 |
| WO | WO 2016/011301 A1 * | 1/2016 |

OTHER PUBLICATIONS

WO 2012006640 Sequence Listing, published Jan. 12, 2012.*
International Search Report and Written Opinion (ISA/US) in International Application No. PCT/US2014/071658, dated May 15, 2015.
Agrawal, A. et al. (2007) "Inhibition of mucin secretion with MARCKS-related peptide improves airway obstruction in a mouse model of asthma," J Appl Physiol 102(1): 399-405.
Arbuzova, A. et al. (2002) "Cross-talk unfolded: MARCKS proteins," Biochem J 362: 1-12.
Chen, C-H. et al. (2013) "Poster Presentations—Cell Migration and invasion 3; Abstract 4919: Myristoylated alanine-rich C kinase substrate (MARCKS) phosphorylation potentials human lung cancer cell malignancy," Cancer Research 73(8) Suppl. 1, abstract.
Chen, C-H. et al. (2014) "A Novel Predictor of Cancer Malignancy: Up-Regulation of Myristoylated Alanine-Rich C Kinase Substrate Phosphorylation in Lung Cancer," American J of Resp and Crit Care Med 189(8): 1002-1004.
Chen, C-H. et al. (2014) "A peptide that inhibits function of Myristoylated Alanine-Rich C Kinase Substrate (MARCKS) reduces lung cancer metastasis," Oncogene 33(28) 3696-3706.
Eckert, R.E. et al. (2010) "Myristoylated Alanine-Rich C-Kinase Substrate (MARCKS) Protein Regulation of Human Neutrophil Migration," Am J Respir Cell Mol Biol 42: 586-94.
Ellena, J.F. et al. (2003) "Location of the myristoylated ananine-rich C-kinase substrate (MARCKS) effector domain in negatively charged phospholipid bicelles," Biophys J 35: 2442-28.

(Continued)

Primary Examiner — Jeffrey E. Russel
(74) Attorney, Agent, or Firm — Foley & Lardner LLP; Antoinette F. Konski

(57) ABSTRACT

This disclosure relates to compositions of isolated polypeptides and methods of their use for the treatment and prevention of disease or disease symptoms associated with MARCKS phosphorylation and/or dissociation from the cell membrane, including but not limited to allergic inflammation, asthma, chronic bronchitis, COPD, infection, hyperreactivity, cystic fibrosis, ulcerative colitis, Crohn's disease, irritable bowel syndrome, rosacea, eczema, psoriasis, acne, arthritis, rheumatoid arthritis, psoriatic arthritis, and systemic lupus erythematosus.

38 Claims, 7 Drawing Sheets
Specification includes a Sequence Listing.

(56) References Cited

OTHER PUBLICATIONS

Elzagallaai, A. et al. (2000) "Platelet secretion induced by phorbol esters stimulation is mediated through phosphorylation of MARCKS: a MARCKS-derived peptide blocks MARCKS phosphorylation and serotonin release without affecting pleckstrin phosphorylation," Blood 95: 894-902.

Gay, E.A. (2008) "Inhibition of native and recombinant nicotinic acetylcholine receptors by the myristoylated alanine-rich C kinase substrate peptide," J Pharmacol Exp Ther 327: 884-90.

Glaser, M. et al. (1996) "Myristoylated alanine-rich C kinase substrate (MARCKS) produces reversible inhibition of phospholipase C by sequestering phosphatidylinositol 4,5-bisphosphate in lateral domains," J Biol Chem 271: 26187-93.

Graff, J.M. et al. (1991) "Protein kinase C substrate and inhibitor characteristics of peptides derived from the myristoylated alanine-rich C kinase substrate (MARCKS) protein phosphorylation site domain," J Biol Chem 266: 14390-98.

Green, T.D. et al. (2011) "Regulation of mucin secretion and inflammation in asthma; A role for MARCKS protein?" Biochim Biophys Acta 1810(11): 1110-1113.

Hinrichsen, R.D. et al. (1993) "Regulation of peptide-calmodulin complexes by protein kinase C in vivo," Proc Natl Acad Sci USA 90: 1585-89.

Kalwa, H. et al. (2011) "The MARCKS protein plays a critical role in phosphatidylinositol 4,5-bisphosphate metabolism and directed cell movement in vascular endothelial cells," J Biol Chem 286: 2320-30.

Li, Y. et al. (2001) "MARCKS Protein is a Key Molecule Regulating Mucin Secretion by Human Airway Epithelial Cells In Vitro," J Biol Chem 276(44): 40982-40990.

Morton, L.A. et al. (2013) "MARCKS-ED peptide as a curvature and lipid sensor," ACS Chem Biol, 8: 218-25.

Park, J-H. et al. (2007) "Protein Kinase C delta Regulates Airway Mucin Secretion via Phosphorylation of MARCKS Protein," Am J Pathol 171(6): 1822-30.

Singer, M. (2004) "A MARCKS-related peptide blocks mucus hypersecretion in a mouse model of asthma," Nat Med 10(2): 193-196.

Theis, T. et al. (2013) "Functional role of the interaction between polysialic acid and myristoylated alanine-rich C kinase substrate at the plasma membrane," J Biol Chem 288: 6726-42.

Timofeeva, O.A. et al. (2010) "Hippocampal infusions of MARCKS peptides impair memory of rats on the radial-arm maze," Brain Res 1308: 147-52.

U.S. Office Action dated Sep. 22, 2017, from U.S. Appl. No. 14/907,539.

Notice of Allowance dated Sep. 7, 2018, from U.S. Appl. No. 14/907,539.

U.S. Office Action dated Apr. 9, 2018, from U.S. Appl. No. 14/907,539.

\* cited by examiner

SUPPRESSION OF ALLERGIC LUNG INFLAMMATION AND HYPERREACTIVITY

CROSS-REFERENCE TO RELATED APPLICATIONS

This application is a national stage application under 35 U.S.C. § 371 of International Application No. PCT/US2014/071658, filed Dec. 19, 2014, which claims the benefit and priority under 35 U.S.C. § 119(e) to U.S. Provisional Application No. 61/919,593, filed Dec. 20, 2013, the content of each of which is hereby incorporated by reference in its entirety.

STATEMENT OF FEDERALLY SPONSORED RESEARCH

This invention was made with government support under Contract Nos. 1 RO1 HL077902 and 1 RO1HL096373 awarded by the National Institutes of Health, National Heart, Lung and Blood Institute (NIH/NHLBI). The government has certain rights in this invention.

SEQUENCE LISTING

The instant application contains a Sequence Listing which has been submitted electronically in ASCII format and is hereby incorporated by reference in its entirety. Said ASCII copy, created on Nov. 30, 2018, is named 060933-5223_SL.txt and is 24,389 bytes in size.

BACKGROUND

Allergic asthma is still a primary public health concern. Airway remodeling, mucous cell metaplasia and persistent inflammation and hyper-reactivity are common features of allergic asthma. Most of these events are regulated by a complex series of interplays between the surrounding cells/tissues and the cytokines/mediators that are present in the airway lumen and walls. Various signaling pathways and mechanisms have been identified and useful for therapeutic application. Despite the progress, treatment of asthma continues to be a challenge, especially in patients with severe and difficult-to-treat asthma and there is a need in the art for effective treatments. This disclosure satisfies this need and related advantages as well.

SUMMARY OF THE DISCLOSURE

Elucidation of the cellular and molecular bases of asthma promises to lead to development of novel strategies for its treatment. Biological agents that specifically target the regulatory or effector cells, or molecules involved in the pathogenesis of asthma, show promise as effective treatment modalities, as Applicants have witnessed in the treatment of other immune-mediated diseases. Among all of these promising developments, one of the treatments focusing on the control of airway mucus granule secretion has provided useful results. This treatment is based on the use of MANS peptide (Singer, M. et al. (2004) Nat Med. 10(2):193-196; Agrawal, A. et al. (2007) J Appl Physiol. 102(1):399-405; Green, T. D. et al. (2011) Biochim Biophys Acta. 1810(11):1110-1113), which is corresponding to the myristoylated N-terminal 24-amino acid portion of the MARCKS (myristoylated alanine-rich C kinase substrates) protein, to compete MARCKS' binding to membrane. Binding to membrane is essential for MARCKS to be phosphorylated by PKC, which is then interactive with F-actin and mucus granules to achieve mucus granule secretion. Despite this demonstration, there is a lack of information regarding to the role of MARCKS in allergic asthma, especially its non-canonical function. Applicants have recently discovered that the non-canonical function of MARCKS rely on its ability to stay in membrane to trap PIP2. This activity is broken if MARCKS is phosphorylated and dissociated from membrane. Applicants constructed an oligopeptide, MPS (SEQ ID NO: 12), corresponding to the MARCKS phosphorylation site domain, that can suppress this non-canonical function and also suppress allergic airway asthma symptoms.

This disclosure provides methods and compositions for one or more of: suppressing MARCKS phosphorylation and/or dissociation from the cell membrane; suppressing or reducing Th2 cytokine (IL-4, IL-5, IL-13 and eotaxin) production and/or IgE level; suppressing mucous metaplasia; inhibiting or suppressing infiltration of inflammatory cells (monocytes, neutrophils, lymphocytes); suppressing and treating allergic inflammation, asthma and hyper-reactivity and disease symptoms associated with each, wherein the compositions for use in the methods comprise a polypeptide comprising at least 6 and no more than 51 amino acids, wherein the amino acid sequence comprises, or alternatively consists essentially of, or alternatively consisting of a polypeptide of at least 6 amino acids to no more than 51 or alternatively 35 amino acids, comprising, or alternatively consisting essentially of, or yet consisting of, XXXRY(S/A/P/G)YXX(S/A/P/G)YX (SEQ ID NO: 1 or 39) and biological equivalents, wherein X is the same or different and is absent or a basic amino acid and Y is the same or different and is absent or a hydrophobic amino acid. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, MPS peptide comprises, or consists essentially of, or yet further aspect, the amino acid sequence (KKKKRF(S/A/P/G)FKK(S/A/P/G)FK) (SEQ ID NO: 2) or KKKKKRF(S/A/P/G)FKK(S/A/P/G)FKL(S/A/P/G)GF(S/A/P/G)FK-KNKK (SEQ ID NO: 3). In one aspect, the polypeptide is at least 6 amino acids and no more than 51 amino acids, or alternatively at least 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, SEQ ID NOS: 1-3 or 39 or biological equivalents of each thereof. In one aspect, a biological equivalent is a polypeptide wherein one or more amino acids have been substituted with a conservative amino acid substitution(s). In one aspect, all serines are replaced by alanine (A-MPSs). In a further aspect, myristic acid is conjugated or joined to the N-terminal amino acid of SEQ ID NOS: 1-3 or 39, including biological equivalents thereof, e.g., wherein all serines are replaced by alanine.

Also provided is an isolated polypeptide and use of the polypeptide in the methods disclosed herein, the polypeptide comprising at least 6 amino acids and no more than 35 amino acids, wherein the amino acid sequence comprises, or alternatively consists essentially of, or alternatively consisting of a polypeptide of no more than 35 amino acids, comprising, or alternatively consisting essentially of, or yet consisting of, XXXRY(S/A/P/G)YXX(S/A/P/G)YX (SEQ ID NO: 1 or 39) and biological equivalents, wherein X is the same or different and is absent or a basic amino acid and Y is the same or different and is absent or a hydrophobic amino acid. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, MPS peptide comprises, or consists essentially of, or yet further aspect, the amino acid sequence (KKKKRF(S/A/P/G)FKK(S/A/P/G)FK) (SEQ ID NO: 2) or KKKKKRF(S/A/P/G)FKK(S/A/P/G)FKL(S/A/P/G)GF(S/A/P/G)FKKNKK (SEQ ID NO: 3) or a biological equivalent thereof. In one aspect, a biological equivalent is a polypeptide wherein one or more amino acids have been substituted with a conservative amino acid substitution. In one aspect, the polypeptide is at least 6 amino acids and no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, SEQ ID NO: 1-3 or 39, or biological equivalents of each thereof. In some embodiments, enhanced efficacy of the disclosed polypeptides to suppress MARCKS phosphorylation and downstream PI3 kinase/AKT pathway activity in different cell types, is desired. Without being bound by theory, Applicant's disclosure provides a modified polypeptide having one or more alanine(s) (A) or glycine(s) (G) substituted for serine (S) to provide this enhanced activity. The present disclosure also provides a modified polypeptide having one or more proline(s) (P) substituted for serine (S). In one aspect, all serines are substituted with alanines (referred to as "A-MPS peptides"). In a further aspect, the MPS polypeptides have myristic acid conjugated or joined to the N-terminal amino acid.

In one aspect of each of the above embodiments, D-MPS (wherein all serines are substituted with aspartate) and myristoylated-wild-type MPS (SEQ ID NO.: 37) are specifically excluded from the group of polypeptides and methods as disclosed herein.

The method also is directed to administration of an antibody or antibody fragment or derivative of each thereof, wherein the antibody, fragment or derivative binds an isolated polypeptide as described herein.

Further provided is an isolated DNA or RNA polynucleotide, wherein the isolated polynucleotide is selected from the group of an isolated polynucleotide encoding the isolated polypeptide, the antibody, the antibody fragment, the antibody derivative, as described above or its respective compliment, or an isolated polynucleotide that has at least 80% sequence identity to the isolated polynucleotide described herein or its complement, or one that hybridizes under conditions of high stringency to the isolated polynucleotide (or its compliment) as described herein, wherein high stringency hybridization conditions is generally performed at about 60° C. in about 1×SSC.

Also provided is an isolated polynucleotide that comprises, or alternatively consists essentially of, or yet further consists of, an anti-MPS siRNA that inhibits the expression of MARCKS, biological equivalents, as well as DNA that encodes the siRNA and the compliment DNA strand and other biological equivalents.

The polynucleotides can be contained with a vector that optionally comprises regulatory sequences operatively linked thereto for the expression and/or replication of the polynucleotides. The appropriate regulatory sequences, e.g., promoters, will vary with the sequence (DNA or RNA) and the use of the polynucleotide. Host cells, e.g., prokaryotic (E. coli or other bacteria), eukaryotic (animal or plant) can comprise the polynucleotides, with or without containment within a vector for expression or replication of the polynucleotides.

Compositions comprising a carrier and one or more of the polypeptides, antibodies, antibody fragments, antibody derivatives, polynucleotides, vectors or host cells are also provided herein.

Polynucleotide encoding the isolated polypeptides, as well as antibodies and fragments thereof that selectively bind to the polypeptides and their equivalents are provided as well as methods for use as disclosed herein. Further provided are polynucleotides that are complementary to the encoding polynucleotides, e.g., mRNA, siRNA or antisense RNA. Vectors or gene delivery vehicles that contain the polynucleotides are provided.

Host cells containing the above noted components are provided, as well as compositions containing the polypeptides, polynucleotides, antibodies, host cells or vectors as described herein.

The polypeptides and useful diagnostically and therapeutically are provided, as described herein.

BRIEF DESCRIPTION OF THE DRAWINGS

FIG. 2A: Murine OVA-allergic model. Balb/C mice at 8 weeks old were sensitized (i.p.) with Ova-Alum, as indicated following the standard protocol. At day 10-14, sensitized mice were intrapertoneal injection (i.p.) injected with MPS (154 µg/mouse/day) or PBS each day (5 times). At day 15-18, sensitized mice were challenged each day with Ova through intra-nasal (i.n.) instillation. At day 19, animals were sacrificed and lung/airway tissues were collected for bronchiolar alveolar lavage (BAL) preparation or directly tissue fixation/processing for paraffin block preparation. FIG. 2B: Immunohistochemical (IHC) characterization of phosphorylated MARCKS in mouse OVA-allergic lung tissue sections. Monoclonal antibody (Mab) against p-Ser-159/163 MARCKS was used for the IHC staining. Tissue sections were from ova-sensitized mice i.p. injected with PBS (saline) or MPS (154 µg/mouse/day) at day 10-14, and exposed (challenged) to PBS or OVA through the intra-nasal (i.n.) instillation. PBS: PBS i.p. and PBS i.n. challenge; MPS: MPS i.p. and PBS i.n.challenge; PBS+OVA: PBS i.p. and OVA i.n. challenge; MPS+OVA: MPS i.p. and OVA i.n. challenge.

FIG. 4A: Lung sections were stained by H&E, and PAS staining. Original magnification ×200. FIG. 4B: Quantification of the numbers of H&E-stained cells and PAS-stained cells, and the score of the Masson trichrome staining are presented in bar graphs. Data are expressed as mean±SEM values (n=6). Black arrows indicate inflammatory cells in H&E, and mucus in PAS in Masson-trichrome-stained lung tissue. # $p<0.05$, compared with the PBS control. *** $p<0.01$, compared with the OVA group.

FIG. 9A shows total CD11C+ CD cells in lungs after ova and peptide treatment. FIG. 9B shows flow cytometry analysis of antigen-presenting DC cells in isolated mediastinal lymph nodes (MLN). FIG. 9C shows total CD11C+ DC in MLN. FIG. 9D shows antigen (ova)-specific 11DC+cells in MLN.

DETAILED DESCRIPTION

Figure 1:
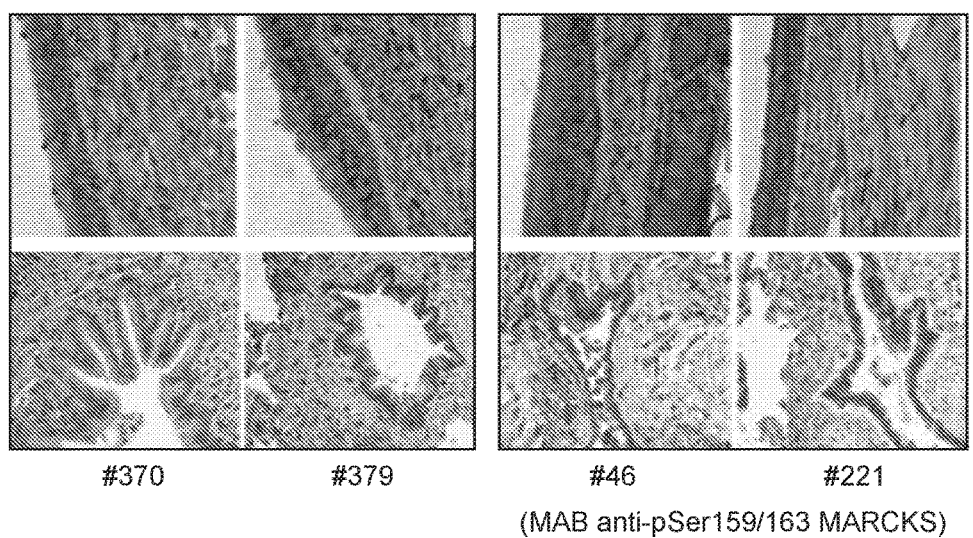
FIG. 1 shows elevated phosphorylated MARCKS is seen in human asthmatic airway tissues. Paraffin sections of human airway tissues from 5 non-asthmatic and 4 asthmatic patients were de-paraffinized and immunohistochemically stained with Mab anti-p-Ser159/163 MARCKS antibody. The control with no primary antibody has no stain (data not included). Representative tissue sections from each non-asthmatic and asthmatic group (indicated by the number at the bottom of the figure) are selected for the presentation. The original magnification is 40×.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; and Mayer and Walker eds. (1987) Immunochemical Methods in Cell and Molecular Biology (Academic Press, London).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

Definitions

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated peptide fragment" is meant to include peptide fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "binding" or "binds" as used herein are meant to include interactions between molecules that may be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

The term "MARCKS" intends the protein that was officially named myristoylated alanine-rich C kinase substrate (MARCKS or MARKS) (Albert, K. A. et al. (1986) Proc. Natl. Acad. Sci. USA 83(9):2822-2826). MARCKS is ubiquitously expressed in various species and tissues (Albert, K. A. et al. (1987) Proc. Natl. Acad. Sci. USA 84(20):7046-7050; Stumpo, D. J. et al. (1989) Proc. Natl. Acad. Sci. USA 86(11):4012-4016), while the other MARCKS family member, MARCKS-related protein (MRP, also known as Mac-MARCKS, F52 or MLP), a 20 kDa protein is highly expressed in brain, reproductive tissues and macrophage (Aderem, A. (1992) Trend. Biochem. Sci. 17(10):438-443; Blacksher, P. J. (1993) J. Biol. Chem. 268:1501-1504). MRP, similar to MARCKS also contains the same three evolutionarily conserved domains; N-terminus myristoylation domain, multiple homology 2 (MH2) domain, and the effector domain (ED). The MH2 domain of unknown function resembles the cytoplasmic tail of the cation-independent mannose-6-phosphate receptor. Protein phosphorylation occurs at $Ser^{159/163}$ of ED domain. The corporation between the N-terminus (myristoylated) and the ED (phosphorylated or not phosphorylated) is essential for controlling the association of these molecules with membranes.

The term "MPS" intends a polypeptide of at least 6 amino acids and no more than 51 amino acids, comprising, or alternatively consisting essentially of, or yet consisting of, XXXRY(S/A/P/G)YXX(S/A/P/G)YX (SEQ ID NO: 1 or 39) and biological equivalents, wherein X is the same or different and is absent or a basic amino acid and Y is the same or different and is absent or a hydrophobic amino acid. In one aspect, the basic amino acid comprises one or more lysine (K), histidine (H) or arginine (R). In one aspect, all X are lysine (K). In one aspect, Y is one or more hydrophobic amino acids, selected from Alanine (A), Isoleucine (I), Leucine (L), Valine (V), Phenylalanine (F), Tryptophan (W) or Tyrosine (Y). In one aspect, all serines are alanine. In another aspect, all X are lysine and all S are substituted with alanine. In a further aspect, all S are Aspartate (D). In a yet further aspect, all of the above noted polypeptides as disclosed herein further comprise, or alternatively consist essentially of, or yet further consist of, myristic acid conjugated or joined to the N-terminal amino acid. In one aspect, MPS peptide comprises, or consists essentially of, or yet further aspect, the amino acid sequence (KKKKRF(S/A/P/G)FKK(S/A/P/G)FK) (SEQ ID NO: 2) or KKKKKRF(S/A/P/G)FKK(S/A/P/G)FKL(S/A/P/G)GF(S/A/P/G)FK-KNKK (SEQ ID NO: 3). In one aspect, the polypeptide is at least 6 amino acids and no more than 51 amino acids, or alternatively at least 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, of SEQ ID NO: 1-3 or 39, or biological equivalents of each thereof. In one aspect, a biological equivalent is a polypeptide wherein one or more amino acids have been substituted with a conservative amino acid substitution. In one aspect, all serines are replaced by alanine (A-MPSs). In a further aspect, myristic acid is conjugated or joined to the N-terminal amino acid of SEQ ID NOS.: 2-3, including biological equivalents thereof, e.g., wherein all serines are replaced by alanine.

The term "MPS" further includes a polypeptide of no more than 51 amino acids, comprising, or alternatively consisting essentially of, or yet consisting of, an isolated polypeptide comprising, or alternatively consisting essentially of, or yet further consisting of, no more than 51 amino acids, wherein the amino acid sequence comprises the amino acid sequence: XXXRYSYXXSYX (SEQ ID NO: 4) or XXXXXRYSYXXSYXLSGYSYXXNXX (SEQ ID NO: 8), and optionally a polynucleotide comprising any contiguous 12 amino acid fragment of SEQ ID NO:8 and biological equivalents of each thereof; and wherein in one aspect, one or more of the serines (S) are substituted with one or more neutral or positively charged amino acids, that may be the same or different, e.g., alanines (A), glycines (G), or prolines (P), or a biological equivalent of each thereof, wherein a biological equivalent of comprises a polypeptide that has at least 80% sequence identity to the above polypeptides or amino acid sequences, or wherein a biological equivalent comprises an isolated polypeptide encoded by an isolated polynucleotide that hybridizes under high stringency conditions to the compliment polynucleotide encoding these polypeptide(s) or the polynucleotide encoding these polypeptides, and wherein high stringency hybridization conditions is generally performed at about 60° C. in about 1×SSC. In one aspect, term also includes the polypeptides having the amino acid sequence XXXRYAYXXAYX (SEQ ID NO: 14) or XXXXXRYAYXXAYXLAGYAYXXNXX (SEQ ID NO.: 15), and optionally a polynucleotide comprising any contiguous 12 amino acid fragment of SEQ ID NO: 15 and biological equivalents thereof; and further optionally wherein one or more serine (S) is substituted with one or more neutral or positively charged amino acids, that may be the same or different, e.g., one or more serines are substituted with one or more alanines (A), glycines (G), or prolines (P), and wherein each X is the same or different and is a basic amino acid and wherein each Y is the same or different and is a hydrophobic amino acid. Non-limiting examples of MPS polypeptides include an isolated polypeptide comprising a biological equivalent of SEQ ID NOs: 4, 8, 14 or 15, which comprises a polypeptide that has at least 80% sequence identity to SEQ ID NOs: 4, 8, 14 or 15, and optionally wherein one or more serine (S) is substituted with one or more neutral or positively charged amino acids, that may be the same or different, e.g., one or more serines are substituted with one or more alanines (A), glycines (G), or prolines (P), and/or wherein a biological equivalent comprises an isolated polypeptide encoded by an an isolated polynucleotide that hybridizes under high stringency conditions to the compliment polynucleotide encoding SEQ ID NOs: 4, 8, 14 or 15, and optionally wherein one or more serine (S) is substituted with one or more neutral or positively charged amino acids, that may be the same or different, e.g., one or more serines are substituted with one or more alanines (A), glycines (G), or prolines (P), and/or the polynucleotide encoding SEQ ID NOs: 4, 8, 14 or 15, and optionally wherein one or more serine (S) is substituted with one or more neutral or positively charged amino acids, that may be the same or different, e.g., one or more serines are substituted with one or more alanines (A), glycines (G), or prolines (P), and wherein high stringency hybridization conditions is generally performed at about 60° C. in about 1×SSC. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptides as described above are no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, the polypeptides of SEQ ID NO: 4, 8, 14 or 15, and optionally wherein one or more serine (S) is substituted with one or more neutral or positively charged amino acids, that may be the same or different, e.g., one or more serines are substituted with one or more alanines (A), glycines (G), or prolines (P), and wherein biological equivalents of each thereof. In one aspect, the MPS peptide comprises, or consists essentially of, an amino acid sequence selected from KKKRFSFKKSFK (SEQ ID NO: 5); KKK-KRFSFKKSFK (SEQ ID NO: 6); KKKR(A/I/L/V/W/Y)S(A/I/L/V/W/Y)KKS(A/I/L/V/W/Y)K (SEQ ID NO: 7); (H/R)$_3$RFSF(H/R)$_2$SF(H/R) (SEQ ID NO: 9); KKKKKR(A/I/L/V/W/Y)S(A/I/L/V/W/Y)KKS(A/I/L/V/W/Y)KLS-GFSFKKNKK (SEQ ID NO: 10); (H/R)$_5$RFSF(H/R)$_2$SF(H/R)LSGFSF(H/R)$_2$N(H/R)$_2$ (SEQ IN NO: 11); KKKKKRFSFKKSFKLSGFSFKKNKK (SEQ ID NO: 12); and optionally a polynucleotide comprising any contiguous 12 amino acid fragment of SEQ ID NO: 12 and biological equivalents thereof; and further optionally wherein one or more serine (S) is substituted with one or more neutral or positively charged amino acids, that may be the same or different, e.g., one or more serines are substituted with one or more alanines (A), for example, KKKKKRFAFKKAF-KLAGFAFKKNKK (SEQ ID NO: 13) and optionally any contiguous 12 amino acid fragment of SEQ ID NO: 13 and biological equivalents thereof; and XXXRYAYXXAYX (SEQ ID NO: 14); XXXXXRYAYXXAYXLAGYAYXX-NXX (SEQ ID NO: 15) and optionally a polynucleotide comprising any contiguous 12 amino acid fragment of SEQ ID NO: 15 and biological equivalents thereof; KKKRFAFK-KAFK (SEQ ID NO: 16), and biological equivalents of each thereof, wherein a biological equivalent of SEQ ID NOs: 4 to 16 (and optionally, wherein one or more serine (S) is substituted with one or more neutral or positively charged amino acids, that may be the same or different, e.g., one or more serines are substituted with one or more alanines (A), glycines (G), or prolines (P)), and comprises a polypeptide that has at least 80% sequence identity to SEQ ID NOs: 4 to 16 and optionally, wherein one or more serine (S) is substituted with one or more neutral or positively charged amino acids, that may be the same or different, e.g., one or more serines are substituted with one or more alanines (A), glycines (G), or prolines (P), and, or wherein a biological equivalent of SEQ ID NOs: 4 to 16 comprises an isolated polypeptide encoded by an isolated polynucleotide that hybridizes under conditions of high stringency to a polynucleotide encoding SEQ ID NOs: 4 to 16, and optionally wherein one or more serine (S) is substituted with one or more neutral or positively charged amino acids, that may be the same or different, e.g., one or more serines are substituted with one or more alanines (A), glycines (G), or prolines (P), respectively or the complement of these polynucleotides encoding the polypeptides, wherein high stringency hybridization conditions is generally performed at about 60° C. in about 1×SSC. A biological equivalent also includes a polypeptide having at least 80% amino acid sequence identity to a polypeptide having an amino acid sequence of SEQ ID NOs: 4 to 16 and optionally wherein one or more serine (S) is substituted with one or more neutral or positively charged amino acids, that may be the same or different, e.g., one or more serines are substituted with one or more alanines (A), glycines (G), or prolines (P).

In a further aspect, an MPS polypeptide comprises an amino acid sequence selected from
XXXRYSYXXSYX (SEQ ID NO: 24);
XXXXRYSYXXSYX (SEQ ID NO: 25);
XXXXXRYSYXXSYX (SEQ ID NO: 26);
XXXXXRYSYXXSYXL (SEQ ID NO: 27);
XXXXXRYSYXXSYXLS (SEQ ID NO: 28);
XXXXXRYSYXXSYXLSG (SEQ ID NO: 29);
XXXXXRYSYXXSYXLSGY (SEQ ID NO: 30);
XXXXXRYSYXXSYXLSGYS (SEQ ID NO: 31);
XXXXXRYSYXXSYXLSGYSY (SEQ ID NO: 32);
XXXXXRYSYXXSYXLSGYSYX (SEQ ID NO: 33);
XXXXXRYSYXXSYXLSGYSYXX (SEQ ID NO: 34);
XXXXXRYSYXXSYXLSGYSYXXN (SEQ ID NO: 35);

XXXXXRYSYXXSYXLSGYSYXXNX (SEQ ID NO: 36), and wherein one or more serine (S) is substituted with one or more neutral or positively charged amino acids, that may be the same or different, wherein in one aspect for each of SEQ ID NOs: 24 to 36, one or more serines is substituted with an alanine, glycine, or proline, and wherein X and Y are as defined above, as well as biological equivalents of each thereof, wherein a wherein a biological equivalent of comprises a polypeptide that has at least 80% sequence identity to the above noted polypeptide amino acid sequences (as well as those noted to be substituted with one or more alanines), or wherein a biological equivalent comprises an isolated polypeptide encoded by an isolated polynucleotide that hybridizes under high stringency conditions to the compliment polynucleotide encoding these polypeptides (as well as those noted to be substituted with one or more alanines), or the polynucleotide encoding these polypeptides (as well as those noted to be substituted with one or more neutral or positively charged amino acids, e.g, alanines, glycines, or prolines), and wherein high stringency hybridization conditions is generally performed at about 60° C. in about 1×SSC.

The MPS polypeptides and biological equivalents have the ability to achieve the same or similar results as noted above. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptide is no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively.

In one aspect, the polypeptides of SEQ ID NOs: 13 and 14, as compared to SEQ ID NOs: 5 and 12, are MPS polypeptides wherein the 4 serine residues of wild-type MPS peptide are replaced by alanine residues, e.g., (KKKK-KRFAFKKAFKLAGFAFKKNKK (SEQ ID NO: 13), that increases membrane affinity. The polypeptides of SEQ ID NO: 13-15 are highly positive charged and interact electrostatically with PIP2 on the phospholipid membrane.

The term "and myristoylated-MPS" intends a sequence of myristic acid—KKKKKRFSFKKSFKLSGFSFKKNKK (SEQ ID NO: 37). One such sequence is disclosed in U.S. Patent Application Publication No. 2009/00220581 (myristic acid-wild type MPS).

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. In one aspect, the polypeptides contain unnatural or synthetic amino acids, including glycine and both the D and L optical isomers of naturally occurring amino acids, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment," as used herein, also refers to a peptide chain.

The phrase "biologically equivalent polypeptide" or "biologically equivalent peptide fragment" refers to protein, polynucleotide, or peptide fragment encoded by a polynucleotide that hybridizes to a polynucleotide encoding the exemplified polypeptide or its complement of the polynucleotide encoding the exemplified polypeptide, under high or moderate stringency and which exhibit similar biological activity in vivo, e.g., approximately 100%, or alternatively, over 90% or alternatively over 85% or alternatively over 70%, as compared to the standard or control biological activity. Additional embodiments within the scope of this invention are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence identity. Percentage identity can be determined by sequence comparison using programs such as BLAST run under appropriate conditions. In one aspect, the program is run under default parameters.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |

-continued

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

The term "polynucleotide" refers to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, or EST), exons, introns, messenger RNA (mRNA), transfer RNA, ribosomal RNA, ribozymes, cDNA, RNAi, siRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component that in one aspect, is a non-naturally occurring combination of polynucleotide and label. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" are synonymously and refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Nov. 26, 2007. Biologically equivalent polynucleotides are those having the specified percent homology and encoding a polypeptide having the same or similar biological activity.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product such as RNA or a polypeptide or protein.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

A "gene product" or alternatively a "gene expression product" refers to the RNA when a gene is transcribed or amino acid (e.g., peptide or polypeptide) generated when a gene is transcribed and translated.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced there from.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge.

A "gene delivery vehicle" is defined as any molecule that can carry inserted polynucleotides into a host cell. Examples of gene delivery vehicles are liposomes, micelles, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Publication Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

As used herein, the term "disease symptom associated with allergic inflammation" intends one associated with the dysfunctional phosphorylation of MARCKS in a cell or tissue. Non-limiting examples of such include asthma, chronic bronchitis, COPD, infection, hyper-reactivity, cystic fibrosis, ulcerative colitis, Crohn's disease, irritable bowel syndrome rosacea, eczema, psoriasis, acne, arthritis, such as rheumatoid arthritis, psoriatic arthritis, systemic lupus erythematosus.

As used herein, the term "hyper-reactivity" in one aspect, intends bronchial hyper-responsiveness or other combinations with airway or hyper-reactivity). This is a state understood characterized by easily triggered bronchospasm. Hyper-reactivity is a symptom of asthma, chronic obstructive pulmonary disease (COPD), infection and cystic fibrosis.

The terms "culture" or "culturing" refer to the in vitro propagation of cells or organisms on or in media of various kinds. It is understood that the descendants of a cell grown in culture may not be completely identical (i.e., morphologically, genetically, or phenotypically) to the parent cell.

A "composition" is intended to mean a combination of active polypeptide, polynucleotide or antibody and another compound or composition, inert (e.g. a detectable label) or active (e.g. a gene delivery vehicle) alone or in combination with a carrier which can in one embodiment be a simple carrier like saline or pharmaceutically acceptable or a solid support as defined below.

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are arrayed on a gene chip for determining the DNA sequence by the hybridization approach, such as that outlined in U.S. Pat. Nos. 6,025,136 and 6,018,041. The polynucleotides of this invention can be modified to probes, which in turn can be used for detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarrays" and similar technologies are known in the art. Examples of such include, but are not limited to, LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarrying system that can dispense from 12 to 64 spots onto multiple glass slides (Intelligent Bio-Instruments); Molecular Biology Workstation and Nano-Chip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and Chip-Maker 3 (TeleChem International, Inc.); and GenoSensor (Vysis, Inc.) as identified and described in Heller (2002) Annu. Rev. Biomed. Eng. 4:129-153. Examples of "gene chips" or a "microarrays" are also described in U.S. Patent Application Publication Nos. 2007/0111322, 2007/0099198, 2007/0084997, 2007/0059769 and 2007/0059765 and U.S. Pat. Nos. 7,138,506, 7,070,740, and 6,989,267.

In one aspect, "gene chips" or "microarrays" containing probes or primers homologous to a polynucleotide, polypeptide or antibody described herein are prepared. A suitable sample is obtained from the patient, extraction of genomic DNA, RNA, protein or any combination thereof is conducted and amplified if necessary. The sample is contacted to the gene chip or microarray panel under conditions suitable for hybridization of the gene(s) or gene product(s) of interest to the probe(s) or primer(s) contained on the gene chip or microarray. The probes or primers may be detectably labeled thereby identifying the gene(s) of interest. Alternatively, a chemical or biological reaction may be used to identify the probes or primers which hybridized with the DNA or RNA of the gene(s) of interest. The genotypes or phenotype of the patient is then determined with the aid of the aforementioned apparatus and methods.

Other non-limiting examples of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding protein, peptide, antibody or antigen, or will be able to ascertain the same by use of routine experimentation.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

"Cell," "host cell" or "recombinant host cell" are terms used interchangeably herein. It is understood that such terms refer not only to the particular subject cell but to the progeny or potential progeny of such a cell. The cells can be of any one or more of the type murine, rat, rabbit, simian, bovine, ovine, porcine, canine, feline, equine, and primate, particularly human. Because certain modifications may occur in succeeding generations due to either mutation or environmental influences, such progeny may not, in fact, be identical to the parent cell, but are still included within the scope of the term as used herein.

The terms "disease" and "disorder" are used inclusively and refer to any condition associated with allergic inflammation or hyperreactivity. Non-limiting examples of such include, asthma, COPD, and infection.

"Treating," "treatment," or "ameliorating" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to a disease. A patient may also be referred to being "at risk of suffering" from a disease. This patient has not yet developed characteristic disease pathology, however are known to be predisposed to the disease due to family history, being genetically predispose to developing the disease, or diagnosed with a disease or disorder that predisposes them to developing the disease to be treated.

DESCRIPTIVE EMBODIMENTS

Isolated Polypeptides and Compositions

This disclosure provides an isolated polypeptide comprising at least 6 amino acids and no more than 51 amino acids, wherein the amino acid sequence comprises, or alternatively consists essentially of, or alternatively consisting of XXXRY(S/A/P/G)YXX(S/A/P/G)YX (SEQ ID NO: 1 or 39) and biological equivalents, wherein X is the same or different and is absent or a basic amino acid and Y is the same or different and is absent or a hydrophobic amino acid. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). XXXRY(S/A/P/G)YXX(S/A/P/G)YX (SEQ ID NO: 1 or 39) and biological equivalents, wherein X is absent or a basic amino acid and Y is absent or a hydrophobic amino acid. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, MPS peptide comprises, or consists essentially of, or yet further aspect, the amino acid sequence (KKKKRF(S/A/P/G)FKK(S/A/P/G)FK) (SEQ ID NO: 2) or KKKKKRF(S/A/P/G)FKK(S/A/P/G)FKL(S/A/P/G)GF(S/A/P/G)FKKNKK (SEQ ID NO: 3). In a further aspect, one or more is amino acid is a modified, non-naturally occurring amino acid. In a further aspect, the polypeptide is no more than 51 or alternatively 45, or alternatively, 40, or alternatively 35, or alternatively 30 amino acids, or alternatively 25 amino acids, or alternatively 20 amino acids, or alternatively 15 amino acids or alternatively the sequence (KKKKRF(S/A/P/G)FKK(S/A/P/G)FK) (SEQ ID NO:2). In one aspect, a biological equivalent is a polypeptide wherein one or more amino acids have been substituted with a conservative amino acid substitution.

Also provided is an isolated polypeptide comprising at least 6 and no more than 51 amino acids, wherein the amino acid sequence comprises, or alternatively consists essentially of, or alternatively consisting of a polypeptide that targets the polypeptide to a specific cell type or stabilizes the polypeptide or yet further comprises a transduction domain for facilitated cell entry or tumor targeting domain and an amino acid having the sequence XXXRY(S/A/P/G)YXX(S/A/P/G)YX (SEQ ID NO: 1 or 39) and biological equivalents, wherein X is the same or different and is absent or a basic amino acid and Y is the same or different and is absent or a hydrophobic amino acid. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, MPS peptide comprises, or consists essentially of, or yet further aspect, the amino acid sequence (KKKKRF(S/A/P/G)FKK(S/A/P/G)FK) (SEQ ID NO: 2) or KKKKKRF(S/A/P/G)FKK(S/A/P/G)FKL(S/A/P/G)GF(S/A/P/G)FKKNKK (SEQ ID NO: 3). In a further aspect, one or more is amino acid is a modified, non-naturally occurring amino acid, such as D-lysine. In a further aspect, the polypeptide is no more than 51, or alternatively at least 40, or alternatively at least 35, or alternatively at least 30 amino acids, or alternatively 25 amino acids, or alternatively 20 amino acids, or alternatively 15 amino acids.

In one aspect, the polypeptides include substantially homologous and biologically equivalent polypeptides. Substantially homologous and biologically equivalent peptide fragments intend those having at least 80% homology, or alternatively at least 85% homology, or alternatively at least 90% homology, or alternatively, at least 95% homology or alternatively, at least 98% homology to any one of SEQ ID NOS. 1-3 or 39, each as determined using methods known to those skilled in the art and identified herein, when run under default parameters. In one aspect, a biological equivalent is a polypeptide wherein one or more amino acids have been substituted with a conservative amino acid substitution.

The "MPS" polypeptides also include a polypeptide of at least 6 amino acids and no more than 51 amino acids, comprising, or alternatively consisting essentially of, or yet consisting of, XXXRY(S/A/P/G)YXX(S/A/P/G)YX (SEQ ID NO: 1 or 39) and biological equivalents, wherein X is the same or different and is absent or a basic amino acid and Y is the same or different and is absent or a hydrophobic amino acid. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, MPS peptide comprises, or consists essentially of, or yet further aspect, the amino acid sequence (KKKKRF(S/A/P/G)FKK(S/A/P/G)FK) (SEQ ID NO: 2) or KKKKKRF(S/A/P/G)FKK(S/A/P/G)FKL(S/A/P/G)GF(S/A/P/G)FKKNKK (SEQ ID NO: 3). In one aspect, the polypeptide is at least 6 amino acids and no more than 51 amino acids, or alternatively at least 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, SEQ ID NO: 1-3 or 39, or biological equivalents of each thereof. In one aspect, a biological equivalent is a polypeptide wherein one or more amino acids have been substituted with a conservative amino acid substitution.

The term "MPS" also includes a a polypeptide of no more than 51 amino acids, comprising, or alternatively consisting essentially of, or yet consisting of, an isolated polypeptide comprising, or alternatively consisting essentially of, or yet further consisting of, no more than 51 amino acids, wherein the amino acid sequence comprises the amino acid sequence: XXXRYSYXXSYX (SEQ ID NO: 4) or XXXXXRYSYXXSYXLSGYSYXXNXX (SEQ ID NO: 8), and optionally a polynucleotide comprising any contiguous 12 amino acid fragment of SEQ ID NO:8 and biological equivalents of each thereof; and wherein in one aspect, one or more of the serines (S) are substituted with one or more neutral or positively charged amino acids, that may be the same or different, e.g., alanines (A), glycines (G), or prolines (P) or a biological equivalent of each thereof, wherein a biological equivalent of comprises a polypeptide that has at least 80% sequence identity to the above polypeptides or amino acid sequences, or wherein a biological equivalent comprises an isolated polypeptide encoded by an isolated polynucleotide that hybridizes under high stringency conditions to the compliment polynucleotide encoding these polypeptide(s) or the polynucleotide encoding these polypeptides, and wherein high stringency hybridization conditions is generally performed at about 60° C. in about 1×SSC. In one aspect, term also includes the polypeptides having the amino acid sequences XXXRYAYXXAYX (SEQ ID NO: 14) or XXXXXRYAYXXAYXLAGYAYXXNXX (SEQ ID NO.: 15), and optionally a polynucleotide comprising any contiguous 12 amino acid fragment of SEQ ID NO: 15 and biological equivalents thereof; and further optionally wherein one or more serine (S) is substituted with one or more neutral or positively charged amino acids, that may be the same or different, e.g., one or more serines are substituted with one or more alanines (A), glycines (G), or prolines (P), and wherein each X is the same or different and is a basic amino acid and wherein each Y is the same or different and is a hydrophobic amino acid. Non-limiting examples of MPS polypeptides include an isolated polypeptide comprising a biological equivalent of SEQ ID NOs: 4, 8, 14 or 15, and in one aspect, wherein one or more serine (S) is substituted with one or more neutral or positively charged amino acids, that may be the same or different, e.g., one or more serines are substituted with one or more alanines (A), glycines (G), or prolines (P), and wherein a biological equivalent of SEQ ID NOs: 4, 8, 14 or 15 and optionally wherein one or more serine (S) is substituted with one or more neutral or positively charged amino acids, that may be the same or different, e.g., one or more serines ae substituted with one or more alanines (A), glycines (G), or prolines (P), and comprises a polypeptide that has at least 80% sequence identity to SEQ ID NOs: 4, 8, 14 or 15, and optionally wherein one or more serine (S) is substituted with one or more neutral or positively charged amino acids, that may be the same or different, e.g., one or more serines are substituted with one or more alanines (A), and or wherein a biological equivalent comprises an isolated polypeptide encoded by an an isolated polynucleotide that hybridizes under high stringency conditions to the compliment polynucleotide encoding SEQ ID NOs: 4, 8, 14 or 15, and optionally wherein one or more serine (S) is substituted with one or more neutral or positively charged amino acids, that may be the same or different, e.g., one or more serines are substituted with one or more alanines (A), and or the polynucleotide encoding SEQ ID NOs: 4, 8, 14 or 15, and optionally wherein one or more serine (S) is substituted with one or more neutral or positively charged amino acids, that may be the same or different, e.g., one or more serines are substituted with one or more alanines (A), and wherein high stringency hybridization conditions is generally performed at about 60° C. in about 1×SSC. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptides as described above are no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively, the polypeptides of SEQ ID NO: 4, 8, 14 or 15, and optionally wherein one or more serine (S) is substituted with one or more neutral or positively charged amino acids, that may be the same or different, e.g., one or more serines are substituted with one or more alanines (A), glycines (G), or prolines (P), and wherein biological equivalents of each thereof. In one aspect, the MPS peptide comprises, or consists essentially of, an amino acid sequence selected from
KKKRFSFKKSFK (SEQ ID NO: 5);
KKKKRFSFKKSFK (SEQ ID NO: 6);
KKKR(A/I/L/V/W/Y)S(A/I/L/V/W/Y)KKS(A/I/L/V/W/Y)K (SEQ ID NO: 7);
(H/R)$_3$RFSF(H/R)$_2$SF(H/R) (SEQ ID NO: 9);
KKKKKR(A/I/L/V/W/Y)S(A/I/L/V/W/Y)KKS(A/I/L/V/W/Y)KLSGFSFKKNKK (SEQ ID NO: 10);
(H/R)$_5$RFSF(H/R)$_2$SF(H/R)LSGFSF(H/R)$_2$N(H/R)$_2$ (SEQ IN NO: 11); KKKKKRFSFKKSFKLSGFSFKKNKK (SEQ ID NO: 12);
and optionally a polynucleotide comprising any contiguous 12 amino acid fragment of SEQ ID NO: 12 and biological equivalents thereof; and further optionally wherein one or more serine (S) is substituted with one or more neutral or positively charged amino acids, that may be the same or different, e.g., one or more serines are substituted with one or more alanines (A), for example, KKKKKRFAFKKAFKLAGFAFKKNKK (SEQ ID NO: 13) and optionally any contiguous 12 amino acid fragment of SEQ ID NO: 13 and biological equivalents thereof; and
XXXRYAYXXAYX (SEQ ID NO: 14);
XXXXXRYAYXXAYXLAGYAYXXNXX (SEQ ID NO: 15) and optionally a polynucleotide comprising any contiguous 12 amino acid fragment of SEQ ID NO: 15 and biological equivalents thereof; KKKRFAFKKAFK (SEQ ID NO: 16),
and biological equivalents of each thereof, wherein a biological equivalent of SEQ ID NOs: 4 to 16 (and optionally, wherein one or more serine (S) is substituted with one or more neutral or positively charged amino acids, that may be the same or different, e.g., one or more serines are substituted with one or more alanines (A), glycines (G), or prolines (P)), and comprises a polypeptide that has at least 80% sequence identity to SEQ ID NOs: 4 to 16 and optionally, wherein one or more serine (S) is substituted with one or more neutral or positively charged amino acids, that may be the same or different, e.g., one or more serines are substituted with one or more alanines (A), glycines (G), or prolines (P), and, or wherein a biological equivalent of SEQ ID NOs: 4 to 16 comprises an isolated polypeptide encoded by an isolated polynucleotide that hybridizes under conditions of high stringency to a polynucleotide encoding SEQ ID NOs: 4 to 16, and optionally wherein one or more serine (S) is substituted with one or more neutral or positively charged amino acids, that may be the same or different, e.g., one or more serines are substituted with one or more alanines (A), glycines (G), or prolines (P), respectively or the complement of these polynucleotides encoding the polypeptides, wherein high stringency hybridization conditions is generally performed at about 60° C. in about 1×SSC. A biological equivalent also includes a polypeptide having at least 80% amino acid sequence identity to a polypeptide having an amino acid sequence of SEQ ID NOs: 4 to 16 and optionally wherein one or more serine (S) is substituted with one or more neutral or positively charged amino acids, that may be the same or different, e.g., one or more serines are substituted with one or more alanines (A), glycines (G), or prolines (P).

In a further aspect, an MPS polypeptide comprises an amino acid sequence selected from
XXXRYSYXXSYX (SEQ ID NO: 24);
XXXXRYSYXXSYX (SEQ ID NO: 25);

XXXXXRYSYXXSYX (SEQ ID NO: 26);
XXXXXRYSYXXSYXL (SEQ ID NO: 27);
XXXXXRYSYXXSYXLS (SEQ ID NO: 28);
XXXXXRYSYXXSYXLSG (SEQ ID NO: 29);
XXXXXRYSYXXSYXLSGY (SEQ ID NO: 30);
XXXXXRYSYXXSYXLSGYS (SEQ ID NO: 31);
XXXXXRYSYXXSYXLSGYSY (SEQ ID NO: 32);
XXXXXRYSYXXSYXLSGYSYX (SEQ ID NO: 33);
XXXXXRYSYXXSYXLSGYSYXX (SEQ ID NO: 34);
XXXXXRYSYXXSYXLSGYSYXXN (SEQ ID NO: 35);
XXXXXRYSYXXSYXLSGYSYXXNX (SEQ ID NO: 36), and wherein one or more serine (S) is substituted with one or more neutral or positively charged amino acids, that may be the same or different, wherein in one aspect for each of SEQ ID NOs: 24 to 36, one or more serines is substituted with an alanine, glycine, or proline, and wherein X and Y are as defined above and in one aspect, all X are K and all S are A, as well as biological equivalents of each thereof, wherein a wherein a biological equivalent of comprises a polypeptide that has at least 80% sequence identity to the above noted polypeptide amino acid sequences (as well as those noted to be substituted with one or more, or all alanines), or wherein a biological equivalent comprises an isolated polypeptide encoded by an isolated polynucleotide that hybridizes under high stringency conditions to the compliment polynucleotide encoding these polypeptides (as well as those noted to be substituted with one or more alanines), or the polynucleotide encoding these polypeptides (as well as those noted to be substituted with one or more neutral or positively charged amino acids, e.g, alanines, glycines, or prolines), and wherein high stringency hybridization conditions is generally performed at about 60° C. in about 1×SSC.

The MPS polypeptides and biological equivalents have the ability to achieve the same or similar results as noted above. In one aspect, the basic amino acid comprises one or more lysine (K), histidine (H) or arginine (R). In one aspect, all X are lysine (K). In one aspect, Y is one or more hydrophobic amino acids, selected from alanine (A), isoleucine (I), leucine (L), valine (V), phenylalanine (F), tryptophan (W) or tyrosine (Y). In one aspect, the polypeptide is no more than 45 amino acids, or alternatively 40 amino acids, or alternatively 35 amino acids, or alternatively 30 amino acids, or alternatively no more than 25 amino acids, or alternatively no more than 20 amino acids, or alternatively no more than 15 amino acids or alternatively.

In one aspect, the polypeptides of SEQ ID NOs: 13 and 14, as compared to SEQ ID NOs: 5 and 12, are MPS polypeptides wherein the 4 serine residues of wild-type MPS peptide are replaced by alanine residues, e.g., (KKKK-KRFAFKKAFKLAGFAFKKNKK (SEQ ID NO: 13), that increases membrane affinity. The polypeptides of SEQ ID NO: 13-15 are highly positive charged and interact electrostatically with PIP2 on the phospholipid membrane.

The polypeptides are useful therapeutically to provide one or more of: suppressing MARCKS phosphorylation and/or dissociation from the cell membrane; suppressing or reducing Th2 cytokine (IL-4, IL-5, IL-13 and eotaxin) production and/or IgE level; suppressing mucous metaplasia; inhibiting or suppressing infiltration of inflammatory cells (monocytes, neutrophils, lymphocytes); inhibiting or suppressing the treatment of disease symptoms associated with allergic inflammation or hyper-reactivity. In one aspect, "myristoylated-MPS" intends a sequence of myristic acid—KKKK-KRFSFKKSFKLSGFSFKKNKK (SEQ ID NO: 37), disclosed in U.S. Patent Application Publication No. 2009/00220581 and along with wild type D-MPS—KKKKKRFDFKKDFKLDGFDFKKNKK (SEQ ID NO.: 38) are specifically excluded from use in the methods as disclosed herein.

Yet further provided is an isolated polypeptide as described above, having additional amino acids added onto the carboxyl-terminal end or amino-terminal end of the polypeptides of any one of SEQ ID NOS: 1-36 or 39 (that may or may not be my, that the length of the polypeptide comprises an additional at least 10 amino acids, or alternatively at least 15 amino acids, or alternatively at least 20 amino acids, or alternatively at least 25 amino acids, or alternatively at least 30 amino acids, or alternatively at least 35 amino acids, or alternatively at least 40 amino acids or the addition of amino acids up to a total of 51 amino acids.

It is known to those skilled in the art that modifications can be made to any peptide to provide it with altered properties. Peptide fragments of the invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred. The disclosed polypeptides, in one aspect, contain unnatural amino acids.

It is known to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobic, size, or charge. Methods used to determine the appropriate amino acid to be substituted and for which amino acid are known to one of skill in the art. Non-limiting examples include empirical substitution models as described by Layoff et al. (1978) In Atlas of Protein Sequence and Structure Vol. 5 suppl. 2 (ed. MR. Day off), pp. 345-352. National Biomedical Research Foundation, Washington D.C.; PAM matrices including Day off matrices (Layoff et al. (1978), supra, or JET matrices as described by Jones et al. (1992) Compute. Appl. Basic. 8:275-282 and Gannet et al. (1992) Science 256:1443-1145; the empirical model described by Adak and Hasegawa (1996) J. Mol. Evil. 42:459-468; the block substitution matrices (BLOSSOM) as described by Henrico and Henrico (1992) Proc. Natl. Acad. Sci. USA 89:10915-10919; Poisson models as described by Neil (1987) Molecular Evolutionary Genetics. Columbia University Press, New York.; and the Maximum Likelihood (ML) Method as described by Muller et al. (2002) Mol. Biol. Evil. 19:8-13.

Accordingly, in yet another aspect the isolated peptide fragment may comprise, or alternatively consisting essentially of, or yet further consisting of, a "biologically equivalent" or "biologically active" polypeptide encoded by equivalent polynucleotides as described herein. They may possess at least 60%, or alternatively, at least 65%, or alternatively, at least 70%, or alternatively, at least 75%, or alternatively at least 80%, or alternatively at least 85%, or alternatively at least 90%, or alternatively at least 95% or alternatively at least 98%, identical primary amino acid sequence to the reference polypeptide when compared using sequence identity methods run under default conditions.

Polypeptides comprising, or alternatively consisting essentially of, or yet further consisting of, the amino acid sequences of the invention can be prepared by expressing polynucleotides encoding the polypeptide sequences of this invention in an appropriate host cell. This can be accomplished by methods of recombinant DNA technology known to those skilled in the art. Accordingly, this invention also provides methods for recombinantly producing the polypeptides of this invention in a eukaryotic or prokaryotic host cell, which in one aspect is further isolated from the host cell. The proteins and peptide fragments of this invention also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

The protein and peptide fragments may be operatively linked to a transduction domain for facilitated cell entry. Protein transduction offers an alternative to gene therapy for the delivery of therapeutic proteins into target cells, and methods involving protein transduction are within the scope of the invention. Protein transduction is the internalization of proteins into a host cell from the external environment. The internalization process relies on a protein or peptide which is able to penetrate the cell membrane. To confer this ability on a normally non-transducing protein, the non-transducing protein can be fused to a transduction-mediating protein such as the antennapedia peptide, the HIV TAT protein transduction domain, or the herpes simplex virus VP22 protein. See Ford et al. (2001) Gene Ther.8:1-4. As such the polypeptides of the invention can, for example, include modifications that can increase such attributes as stability, half-life, ability to enter cells and aid in administration, e.g., in vivo administration of the polypeptides of the invention. For example, polypeptides of the invention can comprise, or alternatively consisting essentially of, or yet further consisting of, a protein transduction domain of the HIV TAT protein as described in Schwarze, et al. (1999) Science 285:1569-1572, and exemplified below. In addition or alternatively, the polypeptides include amino acid sequences that target the polypeptide to the cell or tissue to be treated and/or stabilizes the polypeptide.

In a further aspect, any of the proteins or peptides of this invention can be combined with a detectable label such as a dye or chemiluminescent label for ease of detection.

This invention also provides pharmaceutical composition for in vitro and in vivo use comprising, or alternatively consisting essentially of, or yet further consisting of a therapeutically effective amount of the polypeptide that causes at least about 75%, or alternatively at least about 80%, or alternatively at least about 85%, or alternatively at least about 90%, or alternatively at least about 95%, or alternatively at least about 99% effectiveness in the methods provided herein when applied in a molar concentration of less than about 10 micromolar, or alternatively less than about 9 micromolar, or alternatively less than about 8 micromolar, or alternatively less than about 7 micromolar, or alternatively less than about 6 micromolar, or alternatively less than about 5 micromolar, or alternatively less than about 4 micromolar, or alternatively less than about 3 micromolar, or alternatively less than about 2 micromolar, or alternatively less than about 1 micromolar, or alternatively less than about 0.5 micromolar, or alternatively less than about 0.25 micromolar concentration, as compared to a control that does not receive the composition. Comparative effectiveness can be determined by suitable in vitro or in vivo methods as known in the art and described herein.

This invention also provides compositions for in vitro and in vivo use comprising, or alternatively consisting essentially of, or yet further consisting of one or more of the isolated polypeptides described herein and a pharmaceutically acceptable carrier. In one aspect, the compositions are pharmaceutical formulations for use in the therapeutic methods of this invention. In a further aspect, the invention provides a pharmaceutical composition comprising, or alternatively consisting essentially of, or yet further consisting of, the isolated polypeptide in a concentration such that a therapeutically effective amount of the polypeptide or a pharmacological dose of the composition causes at least a 75%, or alternatively at least a 80%, or alternatively at least a 85%, or alternatively at least a 90%, or alternatively at least a 95% or alternatively at least a 97% reduction disease symptoms associated with one or more of: suppressing MARCKS phosphorylation and/or dissociation from the cell membrane; suppressing or reducing Th2 cytokine (IL-4, IL-5, IL-13 and eotaxin) production and/or IgE level; suppressing mucous metaplasia; inhibiting or suppressing infiltration of inflammatory cells (monocytes, neutrophils, lymphocytes); allergic inflammation or hyper-reactivity as compared to any one of SEQ ID NOS: 1-3 or 39.

Isolated Polynucleotides and Compositions

This invention also provides isolated polynucleotides encoding the polypeptides as described above. In one aspect the polynucleotides encode the biological equivalents or the polypeptides. In another aspect, the polynucleotides or their biological equivalents are labeled with a detectable marker or label, such as a dye or radioisotope, for ease of detection.

This invention also provides the complementary polynucleotides to the sequences identified above, their biological equivalents and their complements. Complementarity can be determined using traditional hybridization under conditions of moderate or high stringency. As used herein, the term polynucleotide intends DNA and RNA as well as modified nucleotides. For example, this invention also provides the anti-sense polynucleotide strand, e.g. antisense RNA or siRNA to these sequences or their complements. One can obtain an antisense RNA using the sequences that encode MPS polypeptide, any one of SEQ ID NOS: 1-36 or 39, or equivalents of each thereof, using a methodology known to one of ordinary skill in the art wherein the degeneracy of the genetic code provides several polynucleotide sequences that encode the same polypeptide or the methodology described in Van der Krol, et al. (1988) Bio-Techniques 6:958. In another aspect, the polynucleotides or their biological equivalents are labeled with a detectable marker or label, such as a dye, chemilumenscent label or radioisotope, for ease of detection.

Substantially homologous and biologically equivalent intends those having varying degrees of homology, such as at least 65%, or alternatively, at least 70%, or alternatively, at least 75%, or alternatively at least 80%, or alternatively, at least 85%, or alternatively at least 90%, or alternatively, at least 95%, or alternatively at least 97% homologous as defined above and which encode polypeptides having the biological activity as described herein. It should be understood although not always explicitly stated that embodiments to substantially homologous peptides and polynucleotides are intended for each aspect of this invention, e.g., peptides, polynucleotides and antibodies.

Alternatively, a biological equivalent is a polypeptide encoded by a nucleic acid that hybridizes under stringent conditions to a nucleic acid or complement that encodes the polypeptide or when a polynucleotide, a polynucleotide that hybridizes to the reference polynucleotide or its complement under conditions of high stringency. Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^2$ normally found in a cell. An equivalent polynucleotide is one that hybridizes under stringent conditions to the reference polynucleotide or the complement of the reference polynucleotide, an in one aspect, having similar biological activity as the reference polynucleotide.

The polynucleotides of this invention can be replicated using conventional recombinant techniques. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this invention also provides a process for obtaining the peptide fragments of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

In one aspect, the polynucleotide is RNA and the RNA is short interfering RNA, also known as siRNA. Methods to prepare and screen interfering RNA and select for the ability to block polynucleotide expression are known in the art and non-limiting examples of which are shown below. These interfering RNA are provided by this invention alone or in combination with a suitable vector or within a host cell. Compositions containing the RNAi are further provided. RNAi is useful to knock-out or knock-down select functions in a cell or tissue as known in the art.

siRNA sequences can be designed by obtaining the target mRNA sequence and determining an appropriate siRNA complementary sequence. siRNAs of the invention are designed to interact with a target sequence, meaning they complement a target sequence sufficiently to hybridize to that sequence. An siRNA can be 100% identical to the target sequence. However, homology of the siRNA sequence to the target sequence can be less than 100% as long as the siRNA can hybridize to the target sequence. Thus, for example, the siRNA molecule can be at least 70%, 75%, 80%, 85%, 90%, 95%, 96%, 97%, 98%, 99% or 100% identical to the target sequence or the complement of the target sequence. Therefore, siRNA molecules with insertions, deletions or single point mutations relative to a target may also be used. The generation of several different siRNA sequences per target mRNA is recommended to allow screening for the optimal target sequence. A homology search, such as a BLAST search, should be performed to ensure that the siRNA sequence does not contain homology to any known mammalian gene.

In general, it is preferable that the target sequence be located at least 100-200 nucleotides from the AUG initiation codon and at least 50-100 nucleotides away from the termination codon of the target mRNA (Duxbury (2004) J. Surgical Res. 117:339-344).

Researchers have determined that certain characteristics are common in siRNA molecules that effectively silence their target gene (Duxbury (2004) J. Surgical Res. 117:339-344; Ui-Tei et al. (2004) Nucl. Acids Res. 32:936-48). As a general guide, siRNAs that include one or more of the following conditions are particularly useful in gene silencing in mammalian cells: GC ratio of between 45-55%, no runs of more than 9 G/C residues, G/C at the 5' end of the sense strand; A/U at the 5' end of the antisense strand; and at least 5 A/U residues in the first 7 bases of the 5' terminal of the antisense strand.

siRNA are, in general, from about 10 to about 30 nucleotides in length. For example, the siRNA can be 10-30 nucleotides long, 12-28 nucleotides long, 15-25 nucleotides long, 19-23 nucleotides long, or 21-23 nucleotides long. When an siRNA contains two strands of different lengths, the longer of the strands designates the length of the siRNA. In this situation, the unpaired nucleotides of the longer strand would form an overhang.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. For example, the stem can be 10-30 nucleotides long, 12-28 nucleotides long, 15-25 nucleotides long, 19-23 nucleotides long, or 21-23 nucleotides long.

Tools to assist siRNA design are readily available to the public. For example, a computer-based siRNA design tool is available on the internet at www.dharmacon.com, last accessed on Nov. 26, 2007.

This invention also provides compositions for in vitro and in vivo use comprising, or alternatively consisting essentially of, or yet further consisting of one or more of the isolated polynucleotide as described herein and a pharmaceutically acceptable carrier. In one aspect, the compositions are pharmaceutical formulations for use in the therapeutic methods of this invention. In a further aspect, the invention provides a pharmaceutical composition comprising, or alternatively consisting essentially of, or yet further consisting of, the isolated polynucleotide in a concentration such that a therapeutically effective amount of the or pharmacological dose of the composition causes at least a 75%, or alternatively at least a 80%, or alternatively at least a 85%, or alternatively at least a 90%, or alternatively at least a 95% or alternatively at least a 97% reduction in disease symptoms associated with allergic inflammation or hyperreactivity, as compared to a control that does not receive the composition. Comparative effectiveness can be determined by suitable in vitro or in vivo methods as known in the art and described herein.

Synthesis of dsRNA and siRNA dsRNA and siRNA can be synthesized chemically or enzymatically in vitro as described in Micura (2002) Agnes Chem. Int. Ed. Emgl. 41:2265-2269; Betz (2003) Promega Notes 85:15-18; and Paddison and Hannon (2002) Cancer Cell. 2:17-23. Chemical synthesis can be performed via manual or automated methods, both of which are well known in the art as described in Micura (2002), supra. siRNA can also be endogenously expressed inside the cells in the form of shRNAs as described in Yu et al. (2002) Proc. Natl. Acad. Sci. USA 99:6047-6052; and McManus et al. (2002) RNA 8:842-850. Endogenous expression has been achieved using plasmid-based expression systems using small nuclear RNA promoters, such as RNA polymerase III U6 or H1, or RNA polymerase II U1 as described in Brummelkamp et al. (2002) Science 296:550-553 (2002); and Novarino et al. (2004) J. Neurosci. 24:5322-5330.

In vitro enzymatic dsRNA and siRNA synthesis can be performed using an RNA polymerase mediated process to produce individual sense and antisense strands that are annealed in vitro prior to delivery into the cells of choice as described in Fire et al. (1998) Nature 391:806-811; Donze and Picard (2002) Nucl. Acids Res. 30(10):e46; Yu et al. (2002); and Shim et al. (2002) J. Biol. Chem. 277:30413-30416. Several manufacturers (Promega, Ambion, New England Biolabs, and Stragene) produce transcription kits useful in performing the in vitro synthesis.

In vitro synthesis of siRNA can be achieved, for example, by using a pair of short, duplex oligonucleotides that contain T7 RNA polymerase promoters upstream of the sense and antisense RNA sequences as the DNA template. Each oligonucleotide of the duplex is a separate template for the synthesis of one strand of the siRNA. The separate short RNA strands that are synthesized are then annealed to form siRNA as described in Protocols and Applications, Chapter 2: RNA interference, Promega Corporation, (2005).

In vitro synthesis of dsRNA can be achieved, for example, by using a T7 RNA polymerase promoter at the 5'-ends of both DNA target sequence strands. This is accomplished by using separate DNA templates, each containing the target sequence in a different orientation relative to the T7 promoter, transcribed in two separate reactions. The resulting transcripts are mixed and annealed post-transcriptionally. DNA templates used in this reaction can be created by PCR or by using two linearized plasmid templates, each containing the T7 polymerase promoter at a different end of the target sequence. Protocols and Applications, Chapter 2: RNA interference, Promega Corporation (2005).

RNA can be obtained by first inserting a DNA polynucleotide into a suitable prokaryotic or eukaryotic host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook and Russell (2001) supra. For instance, mRNA can be isolated using various lytic enzymes or chemical solutions according to the procedures set forth in Sambrook and Russell (2001) supra or extracted by nucleic-acid-binding resins following the accompanying instructions provided by manufactures.

In order to express the polynucleotides to encode the polypeptidesdescribed herein, the polynucleotides can be inserted into a vector and delivered into a host cells (e.g., a prokaryotic or eukaryotic cell) for recombinant expression. Examples of such include viral technologies (e.g., retroviral vectors, adenovirus vectors, adeno-associated virus vectors, alphavirus vectors and the like) and non-viral technologies (e.g., DNA/liposome complexes, micelles and targeted viral protein-DNA complexes) as described herein. Once inside the cell of interest, expression of the polynucleotide can be under the control of ubiquitous promoters (e.g., EF-1) or tissue specific promoters (e.g., Calcium Calmodulin kinase 2 (CaMKI) promoter, NSE promoter and human Thy-1 promoter). Alternatively expression levels may controlled by use of an inducible promoter system (e.g. Tet on/off promoter) as described in Wiznerowicz et al. (2005) Stem Cells 77:8957-8961.

Non-limiting examples of promoters include, but are not limited to, the cytomegalovirus (CMV) promoter (Kaplitt et al. (1994) Nat. Genet. 8:148-154), CMV/human ÿ-globin promoter (Mandel et al. (1998) J. Neurosci. 18:4271-4284), NCX1 promoter, ÿMHC promoter, MLC2v promoter, GFAP promoter (Xu et al. (2001) Gene Ther., 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277) and the β-glucuronidase (GUSB) promoter (Shipley et al. (1991) Genetics 10:1009-1018), the human serum albumin promoter, the alpha-1-antitrypsin promoter. To improve expression, other regulatory elements may additionally be operably linked to the transgene, such as, e.g., the Woodchuck Hepatitis Virus Post-Regulatory Element (WPRE) (Donello et al. (1998) J. Virol. 72: 5085-5092) or the bovine growth hormone (BGH) polyadenylation site.

The invention further provides the isolated polynucleotides of this invention operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)), which contains maps, functional properties, commercial suppliers and a reference to GenEMBL accession numbers for various suitable vectors. Preferable, these vectors are capable of transcribing RNA in vitro or in vivo.

Expression vectors containing these nucleic acids are useful to obtain host vector systems to produce the polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced.

Suitable host cells will depend on the vector and can include mammalian cells, animal cells, human cells, simian cells, insect cells, yeast cells, and bacterial cells as described above and constructed using well known methods. See Sambrook and Russell (2001), supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; DEAE-dextran; electroporation; or microinjection. See Sambrook and Russell (2001), supra for this methodology.

The present invention also provides delivery vehicles suitable for delivery of a polynucleotide of the invention into cells (whether in vivo, ex vivo, or in vitro). A polynucleotide of the invention can be contained within a gene delivery vehicle, a cloning vector or an expression vector. These vectors (especially expression vectors) can in turn be manipulated to assume any of a number of forms which may, for example, facilitate delivery to and/or entry into a cell.

In one aspect when polynucleotides encoding two or more peptides, at least one of which is MPS, any one of SEQ ID NOS: 1-36 or 39, or a biological equivalent of each thereof, are intended to be translated and optionally expressed, the polynucleotides encoding the polypeptides may be organized within a recombinant mRNA or cDNA molecule that results in the transcript that expresses on a single mRNA molecule the at least two peptides. This is accomplished by use of a polynucleotide that has the biological activity of an internal ribosome entry site (IRES) located between the polynucleotide encoding the two peptides. IRES elements initiate translation of polynucleotides without the use of a "cap" structure traditionally thought to be necessary for translation of proteins in eukaryotic cells. Initially described in connection with the untranslated regions of individual picornaviruses, e.g., polio virus and encephalomyocarditis virus, IRES elements were later shown to efficiently initiate translation of reading frames in eukaryotic cells and when positioned downstream from a eukaryotic promoter, it will not influence the "cap"-dependent translation of the first cistron. The IRES element typically is at least 450 nucleotides long when in occurs in viruses and possesses, at its 3' end, a conserved "UUUC" sequence followed by a polypyrimidine trace, a G-poor spacer and an AUG triple.

As used herein, the term "IRES" is intended to include any molecule such as a mRNA polynucleotide or its reverse transcript (cDNA) which is able to initiate translation of the gene downstream from the polynucleotide without the benefit of a cap site in a eukaryotic cell. "IRES" elements can be identical to sequences found in nature, such as the picornavirus IRES, or they can be non-naturally or non-native sequences that perform the same function when transfected into a suitable host cell. Bi- and poly-cistronic expression vectors containing naturally occurring IRES elements are known in the art and described for example, in Pestova et al (1998) Genes Dev. 12:67-83 and International Application No. WO 01/04306, which in turn on page 17, lines 35 to 38 references several literature references which include, but are not limited to Ramesh et al. (1996) Nucl. Acids Res. 24:2697-2700; Pelletier et al. (1988) Nature 334:320-325; Jan et al. (1989) J. Virol. 63:1651-1660; and Davies et al. (1992) J. Virol. 66:1924-1932. Paragraph [0009] of U.S. Patent Appl. Publ. No.: 2005/0014150 A1 discloses several issued U.S. patents wherein a virally-derived IRES element was used to express foreign gene(s) in linear multi-cistronic mRNAs in mammalian cells, plant cells and generally in eukaryotic cells. U.S. Patent Appl. Publ. No. 2004/0082034 A1 discloses an IRES element active in insect cells. Methods to identify new elements also are described in U.S. Pat. No. 6,833,254.

Also within the term "IRES" element are cellular sequences similar to that disclosed in U.S. Pat. No. 6,653,132. The patent discloses a sequence element (designated SP163) composed of sequences derived from the 5'-UTR of VEGF (Vascular Endothelial Growth Factor gene), which, was presumably generated through a previously unknown mode of alternative splicing. The patentees report that an advantages of SP163 is that it is a natural cellular IRES element with a superior performance as a translation stimulator and as a mediator of cap-independent translation relative to known cellular IRES elements and that these functions are maintained under stress conditions.

Further within the term "IRES" element are artificial sequences that function as IRES elements that are described, for example, in U.S. Patent Application Publication No. 2005/0059004 A1.

Operatively linked to the IRES element and separately, are sequences necessary for the translation and proper processing of the peptides. Examples of such include, but are not limited to a eukaryotic promoter, an enhancer, a termination sequence and a polyadenylation sequence. Construction and use of such sequences are known in the art and are combined with IRES elements and protein sequences using recombinant methods. "Operatively linked" shall mean the juxtaposition of two or more components in a manner that allows them to junction for their intended purpose. Promoters are sequences which drive transcription of the marker or target protein. It must be selected for use in the particular host cell, i.e., mammalian, insect or plant. Viral or mammalian promoters will function in mammalian cells. The promoters can be constitutive or inducible, examples of which are known and described in the art.

In one aspect, the peptides are transcribed and translated from a separate recombinant polynucleotide and combined into a functional protein in the host cell. This recombinant polynucleotide does not require the IRES element or marker protein although in one aspect, it may be present.

These isolated host cells containing the polynucleotides of this invention are useful in the methods described herein as well as for the recombinant replication of the polynucleotides and for the recombinant production of peptides and for high throughput screening.

Host Cells

Also provided are host cells comprising one or more of the polypeptides, and/or polynucleotides of this invention. Suitable cells containing the inventive polypeptides and/or polynucleotides include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escerichia coli, Salmonella enterica* and *Streptococcus gordonii*. The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis,*

*Yarrowia*, or *Pichia*. See e.g., U.S. Pat. Nos. 4,812,405; 4,818,700; 4,929,555; 5,736,383; 5,955,349; 5,888,768 and 6,258,559.

In addition to species specificity, the cells can be of any particular tissue type such as a somatic or embryonic stem cell such as a stem cell that can or cannot differentiate into a terminally differentiated cell. The stem cell can be of human or animal origin, such as mammalian.

Therapeutic Antibody Compositions

This invention also provides an antibody capable of specifically forming a complex with a polypeptide of this invention, which are useful in the therapeutic methods of this invention. The term "antibody" includes polyclonal antibodies and monoclonal antibodies, antibody fragments, as well as derivatives thereof. The antibodies include, but are not limited to cows, rabbits, goats, mice, rats, hamsters, guinea pigs, sheep, dogs, cats, monkeys, chimpanzees, apes, etc. The antibodies are also useful to identify and purify therapeutic and/or diagnostic polypeptides. Also provided are hybridoma cell lines producing monoclonal antibodies of this invention.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammal's serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, e.g., www.atcc.org, www.lifetech.com., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al., Proc. Natl. Acad. Sci. USA (1996) 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134.

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured there from. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to known methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See, e.g., Russel et al. (2000) Infection and Immunity April 2000: 1820-1826; Gallo et al. (2000) European J. of Immun. 30:534-540; Green (1999) J. of Immun. Methods 231:11-23; Yang et al. (1999) J. of Leukocyte Biology 66:401-410; Yang (1999) Cancer Research 59(6):1236-1243; Jakobovits (1998) Advanced Drug Delivery Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al., (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.)

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Fd segments ($V_H$-$C_H$1-VH-$C_H$1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. (1985) Proc. Natl. Acad. Sci. USA 82:8653 or Spira, et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn, et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

Antibodies can be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, *pseudomonas* exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Compositions for Therapy

One or more of the above compositions, e.g., polypeptide, antibody, antibody fragment, antibody derivative, polynucleotide encoding these, or RNAi, can be further combined with a carrier, a pharmaceutically acceptable carrier or medical device which is suitable for use of the compositions in diagnostic or therapeutic methods. Thus, the compositions comprise, or alternatively consist essentially of, or yet further consists of, one or more of the above compositions described above in combination with a carrier, a pharmaceutically acceptable carrier or medical device.

The carrier can be a liquid phase carrier or a solid phase carrier, e.g., bead, gel, microarray, or carrier molecule such as a liposome. The composition can optionally further comprise at least one further compound, protein or composition.

Additional examples of "carriers" includes therapeutically active agents such as another peptide or protein (e.g., an Fab' fragment) or agent for the treatment of one or more of: suppressing MARCKS phosphorylation and/or dissociation from the cell membrane; suppressing or reducing Th2 cytokine (IL-4, IL-5, IL-13 and eotaxin) production and/or IgE level; suppressing mucous metaplasia; inhibiting or suppressing infiltration of inflammatory cells (monocytes, neutrophils, lymphocytes); a disease or disease symptoms associated with allergic inflammation or hyper-reactivity. For example, a polypeptide or an antibody of this invention, derivative or fragment thereof can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Accordingly, this invention encompasses a large variety of antibody conjugates, bi- and multispecific molecules, and fusion proteins, whether or not they target the same epitope as the antibodies of this invention.

Yet additional examples of carriers are organic molecules (also termed modifying agents) or activating agents, that can be covalently attached, directly or indirectly, to an polypeptide, antibody, antibody fragment, antibody derivative, polynucleotide encoding these, or RNAi, of this disclosure. Attachment of the molecule can improve pharmacokinetic properties (e.g., increased in vivo serum half-life). Examples of organic molecules include, but are not limited to a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane.

Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. A suitable hydrophilic polymer that modifies the antibody of the invention has a molecular weight of about 800 to about 150,000 Daltons as a separate molecular entity. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Examples of such include, but are not limited to n-dodecanoate, n-tetradecanoate, n-octadecanoate, n-eicosanoate, n-docosanoate, n-triacontanoate, n-tetracontanoate, cis-Δ9-octadecanoate, all cis-Δ5,8,11,14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The present invention provides a composition comprising, or alternatively consisting essentially of, or yet further consisting of, at least one polypeptide, antibody, antibody fragment, antibody derivative, polynucleotide encoding these, or RNAi, of this disclosure, suitable for administration in an effective amount to prevent, reduce, delay, inhibit or suppress disease or disease symptoms associated with allergic inflammation or hyperreactivity. The compositions include, for example, pharmaceutical and diagnostic compositions/kits, comprising a pharmaceutically acceptable carrier and at least one polypeptide, antibody, antibody fragment, antibody derivative, polynucleotide encoding these, or RNAi, of this disclosure. As noted above, the composition can further comprise additional therapeutic agents, e.g., additional small molecules or peptides, which in combination, provide multiple therapies tailored to provide the maximum therapeutic benefit. The combined therapies can be formulated into one composition or alternatively formulated separately and administered concurrently or sequentially in therapeutic effective amounts as determined by the treating physician.

As noted above, alternatively, a composition of this invention can be co-administered with other therapeutic agents, such as a small molecule or peptide, whether or not linked to them or administered in the same dosing. They can be co-administered simultaneously with such agents (e.g., in a single composition or separately) or can be administered before or after administration of such agents.

Compositions for Diagnosis and Therapy

One or more of the above compositions can be further combined with a carrier, a pharmaceutically acceptable carrier or medical device which is suitable for use of the compositions in diagnostic or therapeutic methods.

The carrier can be a liquid phase carrier or a solid phase carrier, e.g., bead, gel, gene chip, microarray, or carrier molecule such as a liposome. The composition can optionally further comprise at least one further compound, protein or composition.

Additional examples of "carriers" includes therapeutically active agents such as another peptide or protein (e.g., an Fab' fragment). For example, a polypeptide, an antibody, derivative or fragment thereof can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Additionally, the antibodies or fragments thereof can be linked to the polypeptides of this invention to facilitate targeting to a cell or tissue of choice and/or to stabilize the polypeptide. Accordingly, this invention encompasses a large variety of antibody conjugates, bi- and multispecific molecules, and fusion proteins, whether or not they target the same epitope as the antibodies of this invention.

Yet additional examples of carriers are organic molecules (also termed modifying agents) or activating agents, that can be covalently attached, directly or indirectly, to an antibody of this invention. Attachment of the molecule can improve pharmacokinetic properties (e.g., increased in vivo serum half-life). Examples of organic molecules include, but are not limited to a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane.

Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. A suitable hydrophilic polymer that modifies the antibody of the invention has a molecular weight of about 800 to about 150,000 Daltons as a separate molecular entity. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Examples of such include, but are not limited to n-dodecanoate, n-tetradecanoate, n-octadecanoate, n-eicosanoate, n-docosanoate, n-triacontanoate, n-tetracontanoate, cis-Δ9-octadecanoate, all cis-Δ5,8,11, 14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

Also provided is a composition containing at least one polypeptide, antibody, antibody fragment, antibody derivative, polynucleotide encoding these, or RNAi, of this disclosure. The compositions include, for example, pharmaceutical and diagnostic compositions/kits, comprising a pharmaceutically acceptable carrier and at least one polypeptide, antibody, antibody fragment, antibody derivative, polynucleotide encoding these, or RNAi, of this disclosure. As noted above, the composition can further comprise additional therapeutic agents e.g., small molecule or peptide, which in combination, provide multiple therapies tailored to provide the maximum therapeutic benefit.

Alternatively, a composition of this invention can be co-administered with other therapeutic agents, whether or not linked to them or administered in the same dosing. They can be co-administered simultaneously with such agents (e.g., in a single composition or separately) or can be administered before or after administration of such agents. Diagnostic Methods Utilizing Recombinant DNA Technology and Bioinformatics The polynucleotides of this invention can be attached to a solid support such as an array or high density chip for use in high throughput screening assays using methods known in the art. For example, the polynucleotide encoding MPS as described above, e.g, any one of SEQ ID NOS: 1-3 or 39, or a biological equivalent of each thereof can be used as a probe to identify expression in a subject sample. They can be attached to chips and the chips can be synthesized on a derivatized glass surface using the methods disclosed in U.S. Pat. Nos. 5,405,783; 5,412,087 and 5,445,934. Photoprotected nucleoside phosphoramidites can be coupled to the glass surface, selectively deprotected by photolysis through a photolithographic mask, and reacted with a second protected nucleoside phosphoramidite. The coupling/deprotection process is repeated until the desired probe is complete.

One can use chemical synthesis to provide the isolated polynucleotides of the present invention. Chemical synthesis of polynucleotides can be accomplished using a number of protocols, including the use of solid support chemistry, where an oligonucleotide is synthesized one nucleoside at a time while anchored to an inorganic polymer. The first nucleotide is attached to an inorganic polymer using a reactive group on the polymer which reacts with a reactive group on the nucleoside to form a covalent linkage. Each subsequent nucleoside is then added to the first nucleoside molecule by: 1) formation of a phosphite linkage between the original nucleoside and a new nucleoside with a protecting group; 2) conversion of the phosphite linkage to a phosphate linkage by oxidation; and 3) removal of one of the protecting groups to form a new reactive site for the next nucleoside as described in U.S. Pat. Nos. 4,458,066; 5,153, 319; 5,132,418; 4,973,679 all of which are incorporated by reference herein. Solid phase synthesis of oligonucleotides eliminates the need to isolate and purify the intermediate products after the addition of every nucleotide base. Following the synthesis of RNA, the oligonucleotides is deprotected (U.S. Pat. No. 5,831,071) and purified to remove by-products, incomplete synthesis products, and the like.

U.S. Pat. No. 5,686,599, describes a method for one pot deprotection of RNA under conditions suitable for the removal of the protecting group from the 2' hydroxyl position. U.S. Pat. No. 5,804,683, describes a method for the removal of exocyclic protecting groups using alkylamines. U.S. Pat. No. 5,831,071, describes a method for the deprotection of RNA using ethylamine, propylamine, or butylamine. U.S. Pat. No. 5,281,701, describes methods and reagents for the synthesis of RNA using 5'-O-protected-2'-O-alkylsilyl-adenosine phosphoramidite and 5'-O-protected-2'-O-alkylsilylguanosine phosphoramidite monomers which are deprotected using ethylthiotetrazole. Usman and Cedergren (1992) Trends in Biochem. Sci. 17:334-339 describe the synthesis of RNA-DNA chimeras for use in studies of the role of 2' hydroxyl groups. Sproat et al. (1995) Nucleosides & Nucleotides 14:255-273, describe the use of 5-ethylthio-1H-tetrazole as an activator to enhance the quality of oligonucleotide synthesis and product yield. Gait et al. (1991) Oligonucleotides and Analogues, ed. F. Eckstein, Oxford University Press 25-48, describe general methods for the synthesis of RNA. U.S. Pat. Nos. 4,923,901; 5,723,599; 5,674,856; 5,141,813; 5,419,966; 4,458,066; 5,252,723; Weetall et al. (1974) Methods in Enzymology 34:59-72; Van Aerschot et al. (1988) Nucleosides and Nucleotides 7:75-90; Maskos and Southern (1992) Nucleic Acids Research 20: 1679-1684; Van Ness et al. (1991) Nucleic Acids Research 19:3345-3350; Katzhendler et al. (1989) Tetrahedron 45:2777-2792; Hovinen et al. (1994) Tetrahedron 50:7203-7218; GB 2,169,605; EP 325,970; PCT International Application Publication No. WO 94/01446; German Patent No. 280,968; and BaGerman Patent No. 4,306,839, all describe specific examples of solid supports for oligonucleotide synthesis and specific methods of use for certain oligonucleotides. Additionally, methods and reagents for oligonucleotide synthesis as known to one of skill in the art as describe by U.S. Pat. No. 7,205,399, incorporated herein by reference in its entirety.

The probes and high density oligonucleotide probe arrays also provide an effective means of monitoring expression of a multiplicity of genes, one of which includes the gene expressing MPS. Thus, the expression monitoring methods can be used in a wide variety of circumstances including detection of disease, identification of differential gene expression between samples isolated from the same patient over a time course, or screening for compositions that upregulate or downregulate the expression of the MPS gene at one time, or alternatively, over a period of time.

Detectable labels suitable for use in the present invention include those identified above as well as any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^3$H, $^{125}$I, $^{35}$S, $^{14}$C or $^{32}$P) enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are known to those of skill in the art. Thus, for example, radiolabels may be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

PCT International Application Publication No. WO 97/10365 describes methods for adding the label to the target (sample) nucleic acid(s) prior to or alternatively, after the hybridization. These are detectable labels that are directly attached to or incorporated into the target (sample) nucleic acid prior to hybridization. In contrast, "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids, see Laboratory Techniques In Biochemistry And Molecular Biology, Vol. 24: Hybridization with Nucleic Acid Probes, P. Tijssen, ed. Elsevier, N.Y. (1993).

The nucleic acid sample also may be modified prior to hybridization to the high density probe array in order to reduce sample complexity thereby decreasing background signal and improving sensitivity of the measurement using the methods disclosed in PCT International Application Publication No. WO 97/10365.

Results from the chip assay are typically analyzed using a computer software program. See, for example, EP 0717 113 A2 and WO 95/20681. This information is compared against existing data sets of gene expression levels for diseased and healthy individuals. A correlation between the obtained data and that of a set of diseased individuals indicates the onset of a disease in the subject patient.

Methods to Identify Therapeutic Agents

The present invention also provides methods to identify leads and methods for treating the disease or disease symptoms associated with one or more of: suppressing MARCKS phosphorylation and/or dissociation from the cell membrane; suppressing or reducing Th2 cytokine (IL-4, IL-5, IL-13 and eotaxin) production and/or IgE level; suppressing mucous metaplasia; inhibiting or suppressing infiltration of inflammatory cells (monocytes, neutrophils, lymphocytes); allergic inflammation or hyper-reactivity. In one aspect, the screen identifies lead compounds or biologics agents that mimic the polypeptides identified above and which are useful to treat these disorders or to treat or ameliorate the symptoms associated with the disorders. Test substances for screening can come from any source. They can be libraries of natural products, combinatorial chemical libraries, biological products made by recombinant libraries, etc. The source of the test substances is not critical to the invention. The present invention provides means for screening compounds and compositions which may previously have been overlooked in other screening schemes.

For the purposes of this invention, an "agent" is intended to include, but not be limited to a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies. They can be administered concurrently or sequentially.

Methods of Use of Polypeptides and Their Compositions

Applicants have discovered that the polypeptides of this invention suppress, prevent, reduce, delay, or inhibit one or more of: MARCKS phosphorylation and/or dissociation from the cell membrane; Th2 cytokine (IL-4, IL-5, IL-13 and eotaxin) production and/or IgE level; mucous metaplasia; infiltration of inflammatory cells (monocytes, neutrophils, lymphocytes); allergic inflammation, asthma, hyper-reactivity or symptoms associated with such. Thus, methods to achieve such in vitro or in vivo are provided by contacting or administering an effective amount of the polypeptide or other therapeutic composition of this invention (e.g., antibody) to a subject in need of such treatment. Administration can be by any suitable method and effective amounts can be empirically determined by a treating physician.

In therapeutic applications, a pharmaceutical composition containing one or more polypeptide or other therapeutic composition (e.g., antibody) described herein is administered to a patient suspected of, or already suffering from allergic inflammation, asthma or hyper-reactivity, wherein said composition is administered in an amount sufficient to cure, or at least partially arrest, the symptoms of the disease (biochemical, histological and/or behavioral), including its complication and intermediate pathological phenotypes in development of the disease. In one aspect, administration is by inhalation, intraperitoneal injection or oral.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the polypeptide of this invention to provide the therapeutic benefit in vitro or in vivo by at least 10%, 25%, 40%, 60%, 80%, 90% or 95% as compared to control. Determination of these parameters is well within the skill of the art. These considerations, as well as effective formulations and administration procedures are well known in the art and are described in standard textbooks.

The "therapeutically effective amount" will vary depending on the polypeptide, the disease and its severity and the age, weight, etc., of the patient to be treated all of which is within the skill of the attending clinician. It is contemplated that a therapeutically effective amount of a polypeptide described herein will provide the therapeutic benefit to the patient as compared to the absence of treatment. As such, tumor growth is suppressed or decreased. A therapeutically effective amount is distinguishable from an amount having a biological effect (a "biologically effective amount"). A biological effect, however, may not result in any clinically measurable therapeutically effect as described above as determined by methods within the skill of the attending clinician.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell, solid tumor or cancer being treated, and the subject being treated. Single or multiple administrations can be carried out with the dose level and pattern being selected by the treating physician. Suitable dosage formulations and methods of administering the agents can be found below.

The pharmaceutical compositions can be administered by inhalation, orally, intranasally, parenterally, injection, orally and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parenteral (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents.

Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier that constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound that enhances absorption or penetration of the agent through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the agent, such carriers as are known in the art to be appropriate.

Formulations suitable for nasal administration or aerosol (directly into the lung), wherein the carrier is a solid, include a coarse powder having a particle size, for example, in the range of about 20 to about 500 microns which is administered as a dry powder or in an inhaler device by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

The following examples are intended to illustrate, and not limit, the inventions disclosed herein.

I. MARCKS Phosphorylation is Elevated in Human Asthmatic Airways

Applicants first examined if MARCKS phosphorylation is elevated in asthmatic tissues. As shown in FIG. 1, immunohistochemical staining with anti-p-MARCKS monoclonal antibody (Mab) demonstrated an increase of immuno-stains in airway epithelial cells in these human asthmatic tissues as compared to non-asthmatic ones. The elevated stains (yellow brown color) were seen in all lining epithelia of respiratory tracts from trachea (FIG. 1, upper) down to the bronchiolar regions (FIG. 1, lower).

Figure 2A:
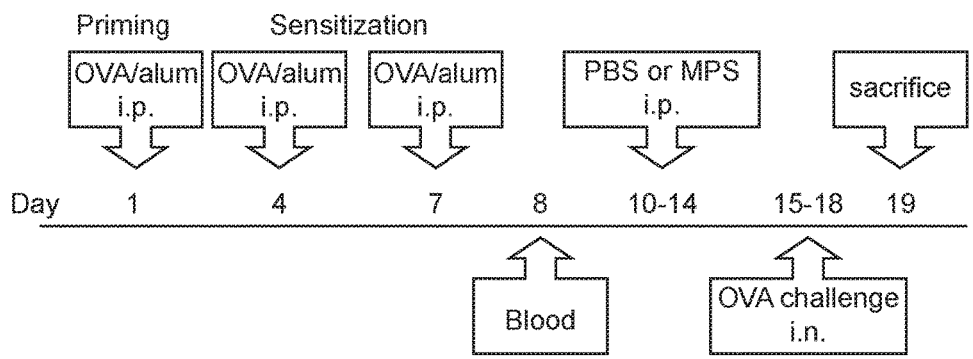
FIGS. 2A-2B shows elevated MARCKS phosphorylation is seen in mouse OVA-allergic airways, but this elevation is suppressed by MPS treatment prior to OVA exposure (challenging phase).
Figure 2B:
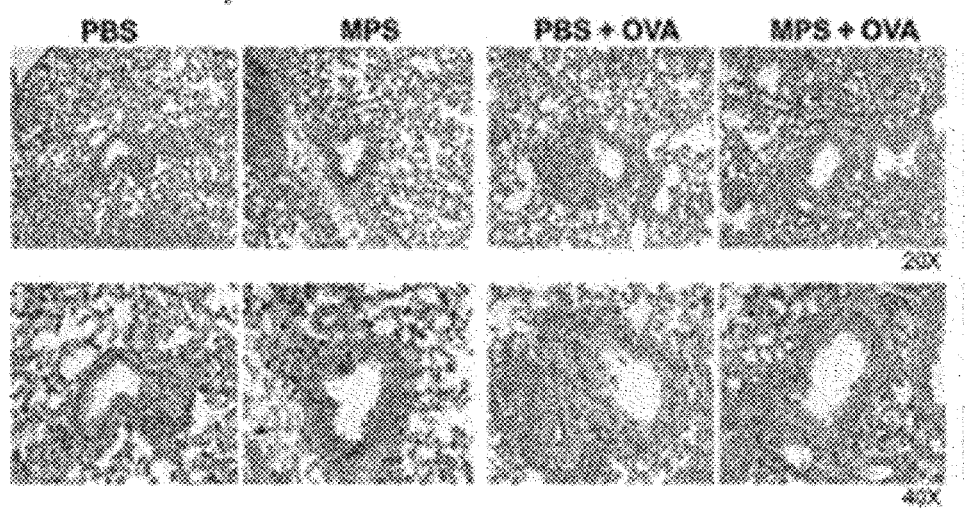

II. MARCKS Phosphorylation is Also Elevated in Mouse Allergic Airways: An In Vivo Ovalbumin (OVA) Allergic Model To extend the above finding in human tissues, Applicants carried out this study in a mouse ovalbumin allergic asthma model (FIG. 2A). As shown in FIG. 2B, tissue sections obtained from the ova-allergic mouse have shown an elevation of immune-stain of phosphorylated MARCKS, while the control, non-allergic airways have much lower stain. These results are consistent with human tissue sections, suggesting a close association of elevated MARCKS phosphorylation with allergic airways. This novel finding may suggest therapeutic target of MARCKS phosphorylation for the treatment of allergic asthma in airways.

Figure 3:
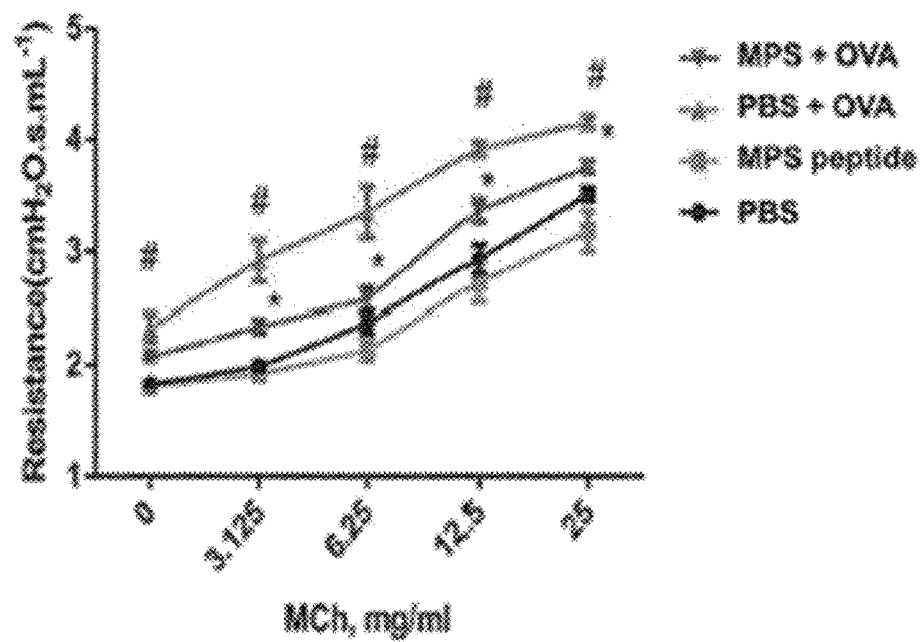
FIG. 3 shows MPS suppressed airway hyper-reactivity of OVA-allergic mouse airways. Experiments were carried out as described in FIG. 2A. At day 19, animals were collected for airway resistance as measured by invasive body plethysmography. Data are expressed as the mean±SEM values (n=3). # $p<0.05$, PBS+OVA compared with the PBS control. * $p<0.05$, MPS+OVA compared with the PBS+OVA group.
Figure 4A:
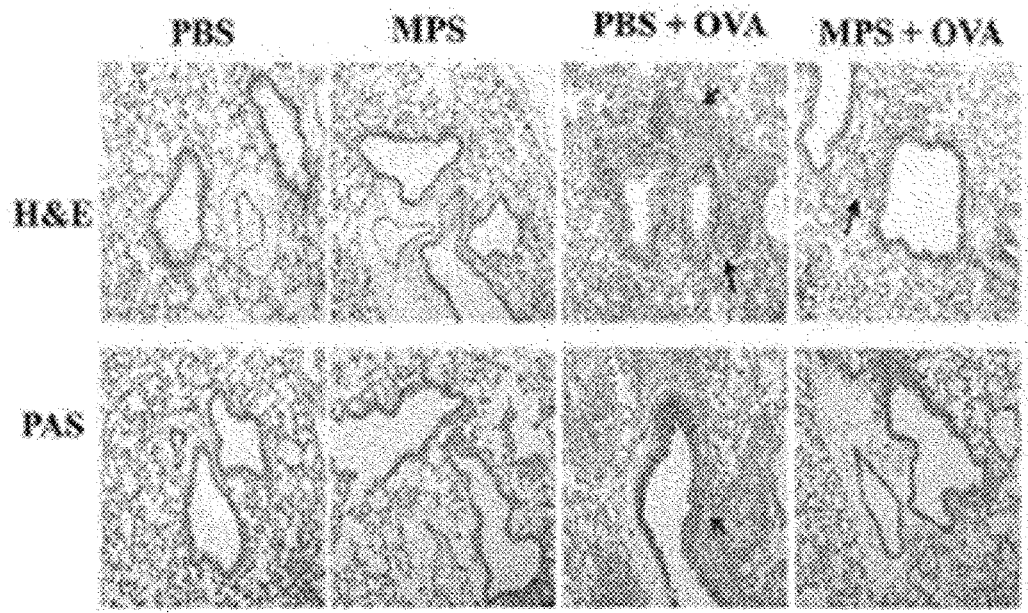
FIGS. 4A-4B show MPS suppressed mucous cell metaplasia (stained by periodic acid stain (PAS)) and inflammatory cells in OVA-allergic mouse airways. Experiments were carried out as described in FIG. 2A. At day 19, animals were sacrificed and lung tissues were fixed for paraffin sections.
Figure 4B:
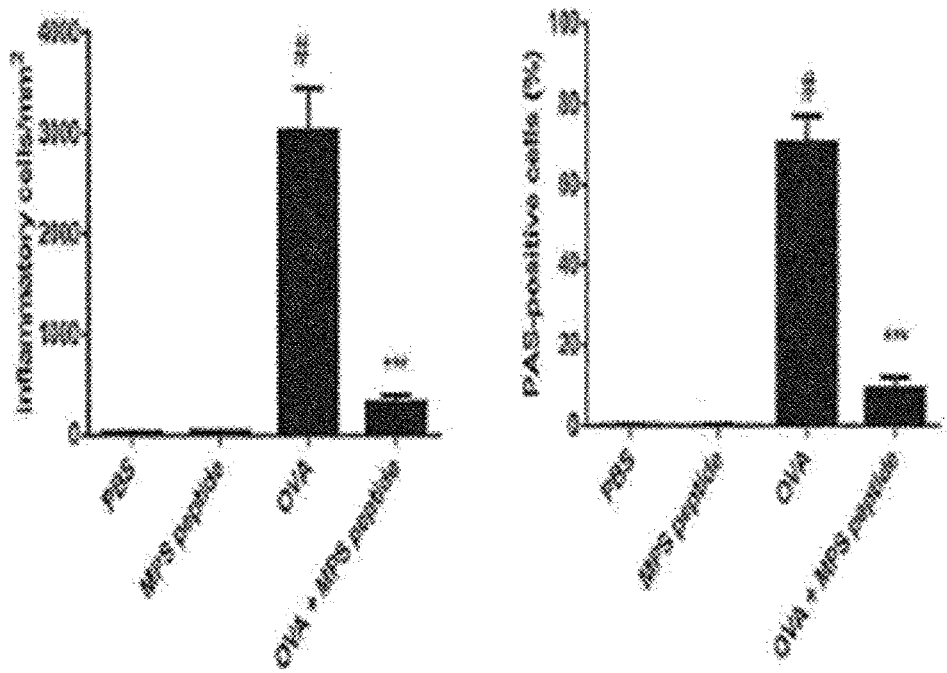
Figure 5:
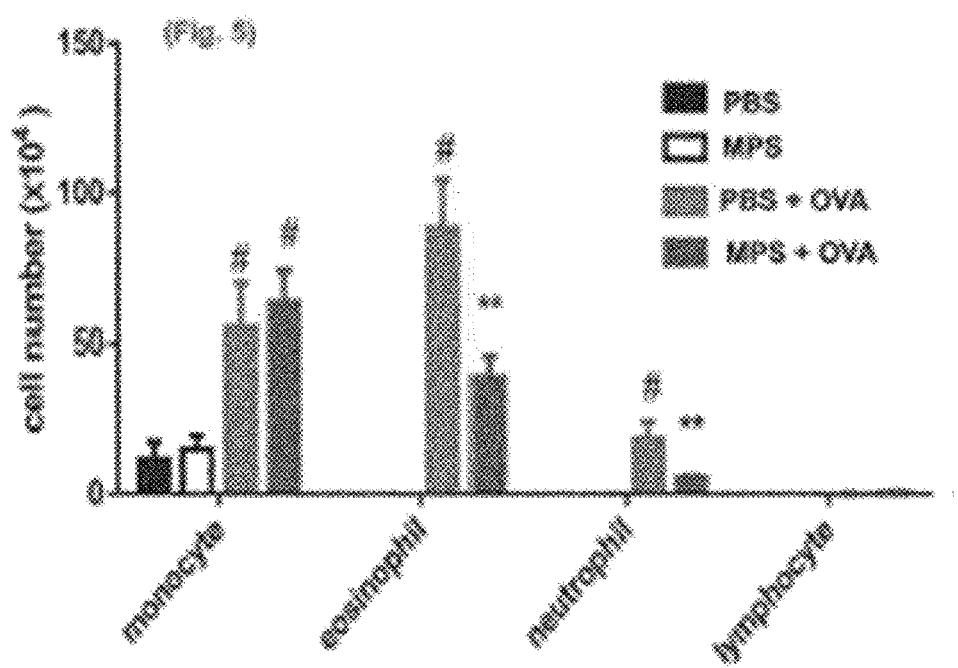
FIG. 5 shows MPS suppressed the presence of various inflammatory cell types in OVA-allergic mouse airways. Experiments were carried out as described in FIG. 2A. At day 19 after OVA (or PBS, control) challenge, mouse airways were harvested and bronchial alveolar lavage fluids (BALFs) were prepared. total cell counts were determined from 3 mL of BALF, and differential cell counts were assessed by Wright and Giemsa staining. Data are expressed as the mean±SEM values (n=6). # $p<0.05$, compared with the PBS control. ** $p<0.01$, compared with the OVA group.
Figure 6:
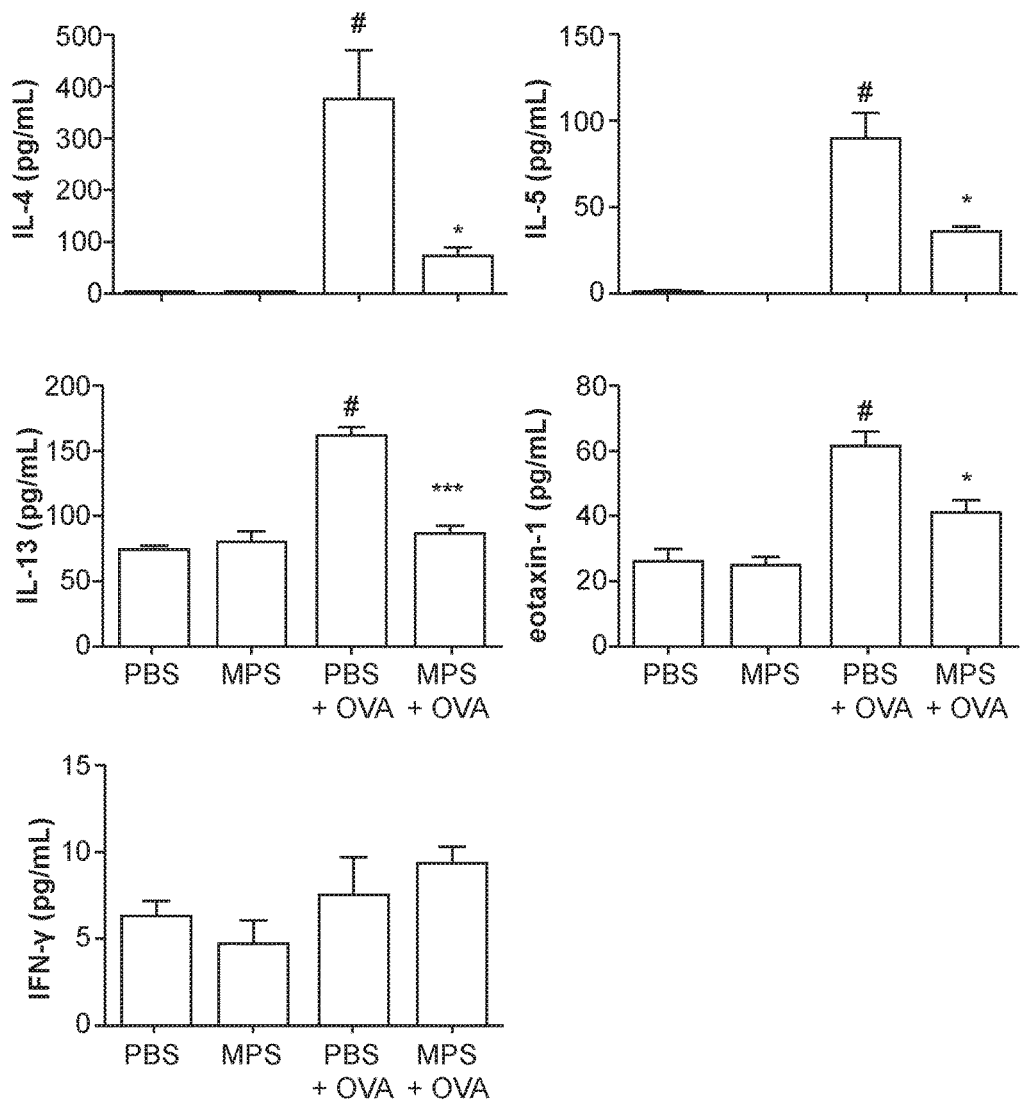
FIG. 6 shows MPS suppressed specifically the Th2 cytokines, but not Th1, in OVA-allergic mouse airways. Experiments were carried out as described in FIG. 2A and BALFs were prepared as described in FIG. 5. Levels of BALF inflammatory cytokines were detected by ELISA. Data are expressed as the mean±SEM. (n=6). #$p<0.05$, compared with the PBS control. *$p<0.05$, ***$p<0.001$, compared with the PBS+OVA group.
Figure 7:
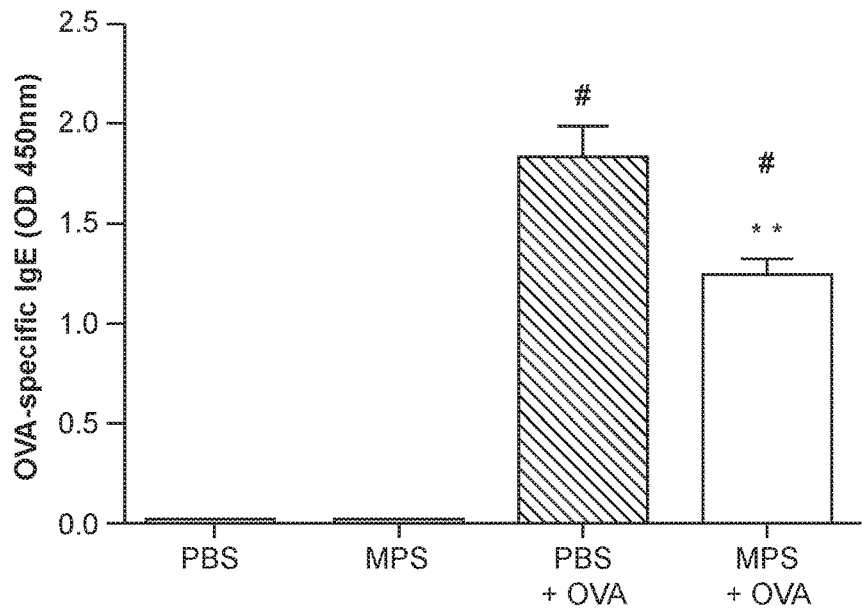
FIG. 7 shows MPS suppressed serum OVA-specific IgE in OVA-allergic mouse. Experiments were carried out as described in FIG. 2A. OVA-specific IgE were detected by ELISA. Data are expressed as the mean±SEM. (n=6). #$p<0.05$, compared with the PBS control. *$p<0.05$, **$p<0.01$, compared with the PBS+OVA group.

III. MPS Peptide is Able to Suppress MARCKS Phosphorylation as Well as the Allergic Symptoms in Mouse OVA-Allergic Airways In Vivo To target MARCKS phosphorylation, Applicants have designed a peptide that is corresponding to MARCKS phosphorylation site (MPS) domain to test this feasibility. As shown in FIG. 2, MPS intraperitoneal (i.p.) injection prior to OVA intra-nasal (i.n.) exposure could effectively suppress MARCKS phosphorylation in these OVA sensitizing mice. This suppression is also seen in the reduction of various allergic symptoms of OVA-allergic mouse airways, such as airway hyper-reactivity (FIG. 3), mucous cell metaplasia (stained with periodic acid staining (PAS)) and the presence of inflammatory cells in respiratory tract tissues (FIG. 4). The reduction of the inflammatory response is very specific for eosinophils (FIG. 5) and Th2 cytokines (IL-4, IL-5,IL-13, and eotaxin), but not the Th1 type (IFN-γ) (FIG. 6). In addition, MPS treatment also suppressed serum OVA-specific IgE level (FIG. 7), a clear indication of the suppression of symptoms associated with allergic asthma by MPS. These results suggest a potential therapeutic application of MPS peptide in the treatment of allergic asthma.

IV. Suppression of Allergic Lung Inflammation and Hyper-Reactivity

Figure 8:
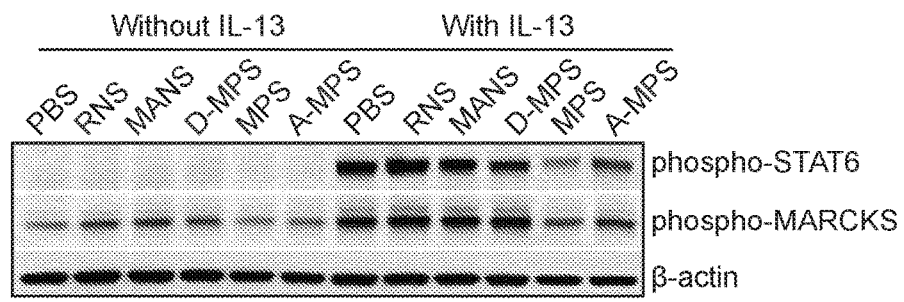
FIG. 8 shows the effects of MPS peptides in the suppression of IL-13-induced signaling pathways in primary normal human bronchial epithelial (NHBE) cells in vitro. Primary NHBE cells were cultured in defined C medium under air-liquid interface condition, as described before (Huang, F. et al. (2008) J Allergy Clin Immunol. 121(6):1415-1421). Fourteen days after the culture, cells were treated with vehicle (PBS), RNS (random MARCKS N-terminal 24-mers sequence), MANS, D-wild-type MPS (KKKKKRFDFK-KDFKLDGFDFKKNKK) (SEQ ID NO: 38), (wild type) MPS (SEQ ID NO.: 12) and A-MPS peptides (50 μM, each) for 4 hrs, then treated with recombinant human IL-13 (20 ng/ml). Cells were harvested one hour later and subjected to protein extraction and western blot analysis. Results have shown IL-13 enhanced both phospho-STAT6 and phospho-MARCKS. These elevations were suppressed by MPS and A-MPS peptide treatments, but not by RNS, MANS and D-MPS peptides. RNS: Random amino acid peptide; MANS: myristoylated 24-mers oligopeptide mimic N-terminal sequence of MARCKS; (wild type) MPS: a 25-mers oligopeptide mimics MARCKS phosphorylation site sequence; A-MPS peptide: a 25-mers oliogopeptide mimics MPS sequence, except all 4 serine residues are replaced by alanine; D-MPS peptide: a 25 mers oligopeptide mimic MPS sequence, except all 4-serine residues are replaced by aspartate residue.
Figure 9A:
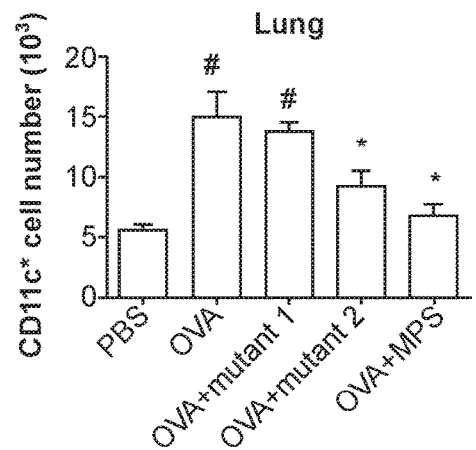
FIGS. 9A-9D show the effects of MPS peptides on the homing of antigen-presenting cells, dendritic cells (DCs) in Ova-induced allergic mouse asthma. For detection of antigen specific DCs migration, mice were challenged with 150 μg OVA-DQ (Life Technologies, Grand Island, N.Y.) for one time per day at day 15-18. Cells were isolated from the mediastinal lymph nodes and lungs. Cells were stained with CD11c conjugated PEC-Cy7 (BD Bioscience, San Jose, Calif.) and analyzed by flow cytometry. Peptides used in this study were (wild type) MPS, A-MPS (mutant 2 in the figure) and D-MPS (mutant 1 in the FIG. 8).
Figure 9B:
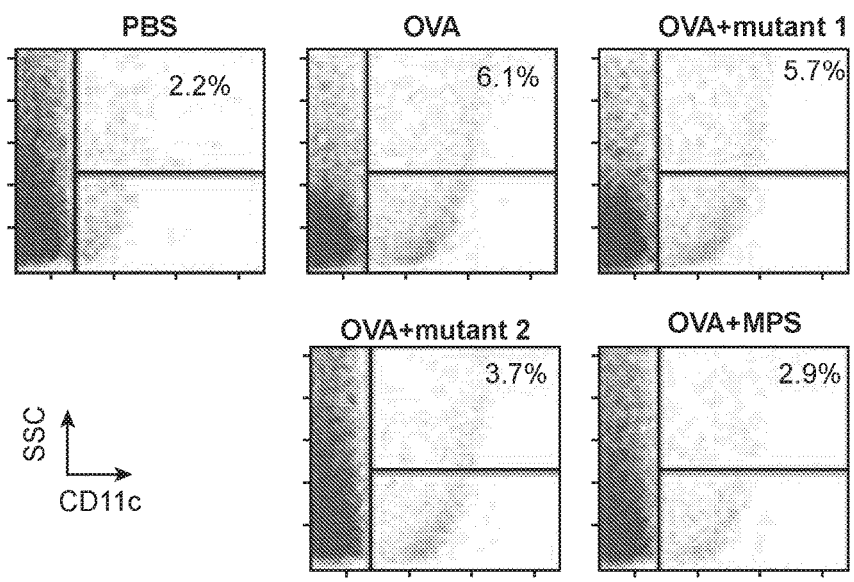
Figure 9C:
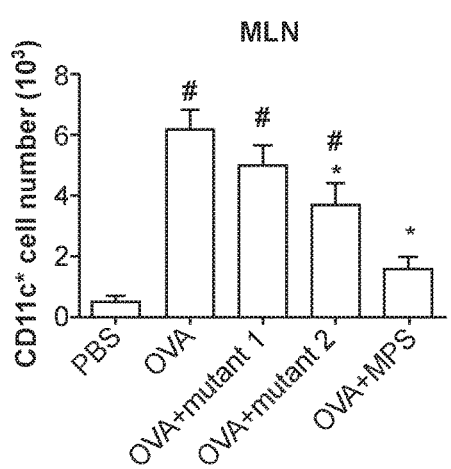
Figure 9D:
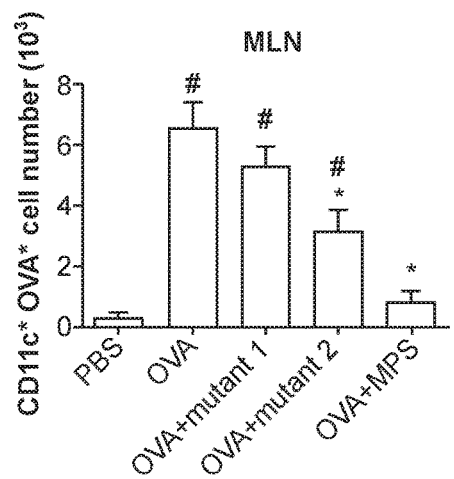

The prior experiments show that the phosphorylated form phospho-MARCKS (p-MARCKS) is elevated in human asthmatic lung tissues as well as from various allergic animal lung/airway tissues, but not in non-asthmatic lung tissues. FIGS. 8 and 9 and the experiments described therein show that the use of (wild-type) MPS and A-MPS peptides, targeting MARCKS' phosphorylation site domain, were able to suppress both the allergic inflammation and airway hyperreactivity associated with the allergen/ovalbumin-induced allergic airway disease in mouse. These suppression effects were not seen with D-MPS peptide, suggesting the specificity and the potential of (wild type) MPS and A-MPS peptides in the suppression of allergic asthma disease symptoms. There are two areas of targeting by both (wild-type) MPS and A-MPS peptides. One is at the airway epithelial cell level. As shown in FIG. 8, IL-13, a major Th2 cytokine associated with asthmatic airway lumen is able to stimulate phospho-STAT6 as well as phospho-MARCKS in airway epithelial cells. Activation of STAT6 phosphorylation is an IL-13 receptor mediated downstream activity upon the binding to IL-13, which is essential for the elevation of eotaxin 3, responsible for Th2 cell type influx to airway lumen. The elevation of phospho-MARCKS by IL-13 has not been reported before, but the in vitro results are consistent with the immunohistochemical study, in which we showed before that phospho-MARCKS is elevated in most of asthmatic tissues and cells. In FIG. 8, the results show that both (wild type) MPS and A-MPS peptides, but not the D-MPS, RNS and MANS, are very effective in the suppression of both IL-13-induced phospho-STAT6 and phospho-MARCKS elevation in human airway epithelial cells.

The second mechanism is the efficacy of (wild type) MARCKS and A-MPS peptides on the suppression of the lymph node homing of antigen-presenting cells to lymph node in allergic animal model. As shown in FIG. 9, lymph node homing of antigen presenting cells is inhibited by (wild type) MPS and A-MPS peptide, while D-MPS peptide and the control treatment have no suppressive effects. Homing antigen-presenting cells to lymph node is a major step in the initiation of various allergic symptoms, such as inflammation, airway remodeling and hyperreactivity, associated with allergic/asthma diseases. The inhibition of lymph node homing is a major mechanism associated with the suppression of allergic/asthmatic airway disease by (wild type) MPS and A-MPS peptides.

The studies described herein are surprising in that it has previously been reported (see U.S. Patent Application Publication No. 2009/00220581) that myristic acid—KKKK-KRFSFKKSFKLSGFSFKKNKK (SEQ ID NO: 37) increased mucus secretion and were believed to bind to endogenous proteins in the cell that competitively inhibit the phosphorylation of MARCKS, thus inhibiting the release of MARCKS from the plasma membrane into the cell interior. Applicant's results show quite the opposite. Applicant's data has shown that there is no need to myristoylate this (wild type) MPS and A-MPS peptides in order anchor to cell membrane since these peptides are cationic and they will be absorbed by the negative charge cell membrane.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for one or more of: preventing, reducing, delaying, inhibiting or suppressing disease or disease symptoms associated with MARCKS phosphorylation in a subject who does not suffer from cancer, comprising administering to the subject an effective amount of any one or more of:
   (a) an isolated polypeptide of any one of:
      SEQ ID NO: 1, wherein an amino acid corresponding to position 6 has been replaced with an alanine, proline, or glycine;
      SEQ ID NO: 2, wherein an amino acid corresponding to position 7 has been replaced with an alanine, proline, or glycine; or
      SEQ ID NO: 3, wherein an amino acid corresponding to position 8 has been replaced with an alanine, proline, or glycine;
   (b) an isolated polynucleotide encoding a polypeptide comprising any one or more of:
      SEQ ID NO: 1, wherein an amino acid corresponding to position 6 has been replaced with an alanine, proline, or glycine;
      SEQ ID NO: 2, wherein an amino acid corresponding to position 7 has been replaced with an alanine, proline, or glycine; or
      SEQ ID NO: 3, wherein an amino acid corresponding to position 8 has been replaced with an alanine, proline, or glycine; or
   (c) a composition comprising any one or more of the polypeptides and polynucleotides of (a) or (b).

2. The method of claim 1, wherein the subject is a mammal.

3. The method of claim 2, wherein the mammal is a canine, murine, feline or a human.

4. The method of claim 1, wherein at least one amino acid present in the isolated polypeptide is a non-naturally occurring amino acid.

5. The method of claim 4, wherein the isolated polypeptide further comprises one or more of: an amino acid sequence to facilitate entry into a cell; a targeting polypeptide; or a polypeptide that confers stability to the polypeptide.

6. The method of claim 1, wherein the isolated polypeptide comprises an MPS polypeptide wherein all serines have been replaced with alanines, prolines, or glycines.

7. The method of claim 1, wherein the isolated polypeptide is administered in a composition comprising a pharmaceutically acceptable carrier.

8. The method of claim 7, wherein the composition is formulated for inhalation therapy.

9. The method of claim 1, wherein the isolated polypeptide is administered locally or systemically.

10. The method of claim 1, wherein the isolated polypeptide is administered locally to the lung.

11. A kit comprising:
(a) an isolated polypeptide of any one of:
SEQ ID NO: 1, wherein an amino acid corresponding to position 6 has been replaced with an alanine, proline, or glycine;
SEQ ID NO: 2, wherein an amino acid corresponding to position 7 has been replaced with an alanine, proline, or glycine; or
SEQ ID NO: 3, wherein an amino acid corresponding to position 8 has been replaced with an alanine, proline, or glycine;
(b) an isolated polynucleotide encoding a polypeptide comprising any one or more of:
SEQ ID NO: 1, wherein an amino acid corresponding to position 6 has been replaced with an alanine, proline, or glycine;
SEQ ID NO: 2, wherein an amino acid corresponding to position 7 has been replaced with an alanine, proline, or glycine; or
SEQ ID NO: 3, wherein an amino acid corresponding to position 8 has been replaced with an alanine, proline, or glycine; or
(c) a composition comprising any one or more of the polypeptides and polynucleotides of (a) or (b).

12. The method of claim 1, wherein the disease or disease symptom associated with MARCKS phosphorylation is allergic inflammation or mucous metaplasia.

13. The method of claim 12, wherein allergic inflammation comprises disease or disease symptoms selected from the group consisting of asthma, chronic bronchitis, chronic obstructive pulmonary disease (COPD), infection, hyperreactivity, cystic fibrosis, ulcerative colitis, Crohn's disease, irritable bowel syndrome, rosacea, eczema, psoriasis, acne, arthritis, rheumatoid arthritis, psoriatic arthritis, and systemic lupus erythematosus.

14. The method of claim 1, wherein the amino acid corresponding to position 10 of SEQ ID NO: 1, position 11 of SEQ ID NO: 2, or position 12 of SEQ ID NO: 3 has been replaced with an alanine, proline, or glycine.

15. The method of claim 4, wherein the non-naturally occurring amino acid is a D-amino acid.

16. The kit of claim 11, wherein the amino acid corresponding to one or more of: position 10 of SEQ ID NO: 1, position 11 of SEQ ID NO: 2, or position 12 of SEQ ID NO: 3 has been replaced with an alanine, proline, or glycine.

17. The kit of claim 11, wherein the polypeptide comprises an MPS polypeptide wherein all serines have been replaced with alanines, prolines, or glycines.

18. A method for one or more of: preventing, reducing, delaying, inhibiting or suppressing disease or disease symptoms associated with MARCKS phosphorylation in a subject in need thereof, comprising administering to the subject an effective amount of any one or more of:
(a) an isolated polypeptide of any one of:
SEQ ID NO: 4, 5, 7, 9, or 24, wherein an amino acid corresponding to position 6 has been replaced with an alanine, proline, or glycine, and optionally wherein an amino acid corresponding to position 10 has been replaced with an alanine, proline, or glycine;
SEQ ID NO: 6 or 25, wherein an amino acid corresponding to position 7 has been replaced with an alanine, proline, or glycine, and optionally wherein an amino acid corresponding to position 11 has been replaced with an alanine, proline, or glycine;
SEQ ID NO: 8, 10, 11, 12, 31, 32, 33, 34, 35, 36, or 37, wherein an amino acid corresponding to position 8 has been replaced with an alanine, proline, or glycine, optionally wherein an amino acid corresponding to position 12 has been replaced with an alanine, proline, or glycine, optionally wherein an amino acid corresponding to position 16 has been replaced with an alanine, proline, or glycine, and optionally wherein an amino acid corresponding to position 19 has been replaced with an alanine, proline, or glycine;
SEQ ID NO: 26 or 27, wherein an amino acid corresponding to position 8 has been replaced with an alanine, proline, or glycine, and optionally wherein an amino acid corresponding to position 12 has been replaced with an alanine, proline, or glycine;
SEQ ID NO: 28, 29, or 30, wherein an amino acid corresponding to position 8 has been replaced with an alanine, proline, or glycine, optionally wherein an amino acid corresponding to position 12 has been replaced with an alanine, proline, or glycine, and optionally wherein an amino acid corresponding to position 16 has been replaced with an alanine, proline, or glycine;
SEQ ID NO: 14 or 16, optionally wherein an amino acid corresponding to position 6 has been replaced with a proline or glycine, and optionally wherein an amino acid corresponding to position 10 has been replaced with a proline or glycine; or
SEQ ID NO: 13 or 15, optionally wherein an amino acid corresponding to position 8 has been replaced with a proline or glycine, optionally wherein an amino acid corresponding to position 12 has been replaced with a proline or glycine, optionally wherein an amino acid corresponding to position 16 has been replaced with a proline or glycine, and optionally wherein an amino acid corresponding to position 19 has been replaced with a proline or glycine; or
(b) an isolated polynucleotide encoding a polypeptide comprising any one or more of:
SEQ ID NO: 4, 5, 7, 9, or 24, wherein an amino acid corresponding to position 6 has been replaced with an alanine, proline, or glycine, and optionally wherein an amino acid corresponding to position 10 has been replaced with an alanine, proline, or glycine;
SEQ ID NO: 6 or 25, wherein an amino acid corresponding to position 7 has been replaced with an alanine, proline, or glycine, and optionally wherein an amino acid corresponding to position 11 has been replaced with an alanine, proline, or glycine;
SEQ ID NO: 8, 10, 11, 12, 31, 32, 33, 34, 35, 36, or 37, wherein an amino acid corresponding to position 8 has been replaced with an alanine, proline, or glycine, optionally wherein an amino acid corresponding to position 12 has been replaced with an alanine, proline, or glycine, optionally wherein an amino acid corresponding to position 16 has been replaced with an alanine, proline, or glycine, and optionally wherein an amino acid corresponding to position 19 has been replaced with an alanine, proline, or glycine;
SEQ ID NO: 26 or 27, wherein an amino acid corresponding to position 8 has been replaced with an alanine, proline, or glycine, and optionally wherein an amino acid corresponding to position 12 has been replaced with an alanine, proline, or glycine;

SEQ ID NO: 28, 29, or 30, wherein an amino acid corresponding to position 8 has been replaced with an alanine, proline, or glycine, optionally wherein an amino acid corresponding to position 12 has been replaced with an alanine, proline, or glycine, and optionally wherein an amino acid corresponding to position 16 has been replaced with an alanine, proline, or glycine;

SEQ ID NO: 14 or 16, optionally wherein an amino acid corresponding to position 6 has been replaced with a proline or glycine, and optionally wherein an amino acid corresponding to position 10 has been replaced with a proline or glycine; or SEQ ID NO: 13 or 15, optionally wherein an amino acid corresponding to position 8 has been replaced with a proline or glycine, optionally wherein an amino acid corresponding to position 12 has been replaced with a proline or glycine, optionally wherein an amino acid corresponding to position 16 has been replaced with a proline or glycine, and optionally wherein an amino acid corresponding to position 19 has been replaced with a proline or glycine; or (c) a composition comprising any one or more of the polypeptides and polynucleotides of (a) or (b); and with the proviso that the subject does not suffer from cancer.

19. The method of claim 18, wherein the subject is a mammal.

20. The method of claim 19, wherein the mammal is a canine, murine, feline or a human.

21. The method of claim 18, wherein at least one amino acid present in the isolated polypeptide is a non-naturally occurring amino acid.

22. The method of claim 21, wherein the isolated polypeptide further comprises one or more of: an amino acid sequence to facilitate entry into a cell; a targeting polypeptide; or a polypeptide that confers stability to the polypeptide.

23. The method of claim 18, wherein the amino acid corresponding to one or more of:

position 10 of SEQ ID NO: 4, 5, 7, 9, or 24 has been replaced with an alanine, proline, or glycine;

position 11 of SEQ ID NO: 6 or 25 has been replaced with an alanine, proline, or glycine;

position 12 of SEQ ID NO: 8, 10, 11, 12, 26, 27, 28, 29, 30, 31, 32, 33, 34, 35, 36, or 37 has been replaced with an alanine, proline, or glycine;

position 10 of SEQ ID NO: 14 or 16 has been replaced with a proline or glycine; or position 12 of SEQ ID NO: 13 or 15 has been replaced with a proline or glycine.

24. The method of claim 18, wherein all serines in SEQ ID NOs.: 8, 10, 11, 12, 28, 29, 30, 31, 32, 33, 34, 35, 36, and 37 have been replaced with alanines, prolines, or glycines.

25. The method of claim 18, wherein the isolated polypeptide is administered in a composition comprising a pharmaceutically acceptable carrier.

26. The method of claim 25, wherein the composition is formulated for inhalation therapy.

27. The method of claim 18, wherein the isolated polypeptide is administered locally or systemically.

28. The method of claim 18, wherein the isolated polypeptide is administered locally to the lung.

29. The method of claim 21, wherein the non-naturally occurring amino acid is a D-amino acid.

30. The method of claim 18, wherein the disease or disease symptom associated with MARCKS phosphorylation is allergic inflammation or mucous metaplasia.

31. The method of claim 30, wherein allergic inflammation comprises disease or disease symptoms selected from the group consisting of asthma, chronic bronchitis, COPD, infection, hyper-reactivity, cystic fibrosis, ulcerative colitis, Crohn's disease, irritable bowel syndrome, rosacea, eczema, psoriasis, acne, arthritis, rheumatoid arthritis, psoriatic arthritis, and systemic lupus erythematosus.

32. The kit of claim 11, wherein at least one amino acid present in the isolated polypeptide is a non-naturally occurring amino acid.

33. The kit of claim 32, wherein the non-naturally occurring amino acid is a D-amino acid.

34. The kit of claim 33, wherein the D-amino acid is D-lysine.

35. The kit of claim 12, wherein the isolated polypeptide is SEQ ID NO: 13.

36. The kit of claim 35, wherein at least one amino acid present in the isolated polypeptide is a non-naturally occurring amino acid.

37. The kit of claim 36, wherein the non-naturally occurring amino acid is a D-amino acid.

38. The kit of claim 37, wherein the D-amino acid is D-lysine.

* * * * *

SEQUENCE LISTING

```
<160> NUMBER OF SEQ ID NOS: 39

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (6)..(6)
<223> OTHER INFORMATION: Ser, Ala, Pro or Gly
<220> FEATURE:
<221> NAME/KEY: MOD_RES
```

```
<222> LOCATION: (7)..(7)
<223> OTHER INFORMATION: Any hydrophobic amino acid
<220> FEATURE:
<221> NAME/KEY: MOD_RES
<222> LOCATION: (8)..(9)
<223> OTHER INFORMATION: Any basic amino acid
<220> FEATURE:
<221> NAME/KEY: MOD_RES
<222> LOCATION: (10)..(10)
<223> OTHER INFORMATION: Ser, Ala, Pro or Gly
<220> FEATURE:
<221> NAME/KEY: MOD_RES
<222> LOCATION: (11)..(11)
<223> OTHER INFORMATION: Any hydrophobic amino acid
<220> FEATURE:
<221> NAME/KEY: MOD_RES
<222> LOCATION: (12)..(12)
<223> OTHER INFORMATION: Any basic amino acid
<220> FEATURE:
<223> OTHER INFORMATION: See specification as filed for detailed
      description of substitutions and preferred embodiments

<400> SEQUENCE: 1

Xaa Xaa Xaa Arg Xaa Xaa Xaa Xaa Xaa Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser, Ala, Pro or Gly
<220> FEATURE:
<221> NAME/KEY: MOD_RES
<222> LOCATION: (11)..(11)
<223> OTHER INFORMATION: Ser, Ala, Pro or Gly

<400> SEQUENCE: 2

Lys Lys Lys Lys Arg Phe Xaa Phe Lys Lys Xaa Phe Lys
1               5                   10

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ser, Ala, Pro or Gly
<220> FEATURE:
<221> NAME/KEY: MOD_RES
<222> LOCATION: (12)..(12)
<223> OTHER INFORMATION: Ser, Ala, Pro or Gly
<220> FEATURE:
<221> NAME/KEY: MOD_RES
<222> LOCATION: (16)..(16)
<223> OTHER INFORMATION: Ser, Ala, Pro or Gly
<220> FEATURE:
<221> NAME/KEY: MOD_RES
<222> LOCATION: (19)..(19)
<223> OTHER INFORMATION: Ser, Ala, Pro or Gly

<400> SEQUENCE: 3

Lys Lys Lys Lys Lys Arg Phe Xaa Phe Lys Lys Xaa Phe Lys Leu Xaa
1               5                   10                  15
```

```
Gly Phe Xaa Phe Lys Lys Asn Lys Lys
            20              25
```

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (8)..(9)
<223> OTHER INFORMATION: Any basic amino acid
<220> FEATURE:
<221> NAME/KEY: MOD_RES
<222> LOCATION: (11)..(11)
<223> OTHER INFORMATION: Any hydrophobic amino acid
<220> FEATURE:
<221> NAME/KEY: MOD_RES
<222> LOCATION: (12)..(12)
<223> OTHER INFORMATION: Any basic amino acid
<220> FEATURE:
<223> OTHER INFORMATION: See specification as filed for detailed
      description of substitutions and preferred embodiments

<400> SEQUENCE: 4

```
Xaa Xaa Xaa Arg Xaa Ser Xaa Xaa Xaa Ser Xaa Xaa
1               5                   10
```

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Lys Lys Lys Arg Phe Ser Phe Lys Lys Ser Phe Lys
1               5                   10
```

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Lys Lys Lys Lys Arg Phe Ser Phe Lys Lys Ser Phe Lys
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (5)..(5)
<223> OTHER INFORMATION: Ala, Ile, Leu, Val, Trp or Tyr
<220> FEATURE:
<221> NAME/KEY: MOD_RES
<222> LOCATION: (7)..(7)
<223> OTHER INFORMATION: Ala, Ile, Leu, Val, Trp or Tyr
<220> FEATURE:
<221> NAME/KEY: MOD_RES
<222> LOCATION: (11)..(11)
<223> OTHER INFORMATION: Ala, Ile, Leu, Val, Trp or Tyr

<400> SEQUENCE: 7

Lys Lys Lys Arg Xaa Ser Xaa Lys Lys Ser Xaa Lys
1               5                   10

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid
<220> FEATURE:
<221> NAME/KEY: MOD_RES
<222> LOCATION: (24)..(25)
<223> OTHER INFORMATION: Any basic amino acid
<220> FEATURE:
<223> OTHER INFORMATION: See specification as filed for detailed
      description of substitutions and preferred embodiments

<400> SEQUENCE: 8

Xaa Xaa Xaa Xaa Xaa Arg Xaa Ser Xaa Xaa Xaa Ser Xaa Xaa Leu Ser
1               5                   10                  15

Gly Xaa Ser Xaa Xaa Xaa Asn Xaa Xaa
            20                  25
```

```
<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: His or Arg
<220> FEATURE:
<221> NAME/KEY: MOD_RES
<222> LOCATION: (8)..(9)
<223> OTHER INFORMATION: His or Arg
<220> FEATURE:
<221> NAME/KEY: MOD_RES
<222> LOCATION: (12)..(12)
<223> OTHER INFORMATION: His or Arg

<400> SEQUENCE: 9

Xaa Xaa Xaa Arg Phe Ser Phe Xaa Xaa Ser Phe Xaa
1               5                   10

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ala, Ile, Leu, Val, Trp or Tyr
<220> FEATURE:
<221> NAME/KEY: MOD_RES
<222> LOCATION: (9)..(9)
<223> OTHER INFORMATION: Ala, Ile, Leu, Val, Trp or Tyr
<220> FEATURE:
<221> NAME/KEY: MOD_RES
<222> LOCATION: (13)..(13)
<223> OTHER INFORMATION: Ala, Ile, Leu, Val, Trp or Tyr

<400> SEQUENCE: 10

Lys Lys Lys Lys Lys Arg Xaa Ser Xaa Lys Lys Ser Xaa Lys Leu Ser
1               5                   10                  15

Gly Phe Ser Phe Lys Lys Asn Lys Lys
            20                  25

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: His or Arg
<220> FEATURE:
<221> NAME/KEY: MOD_RES
<222> LOCATION: (10)..(11)
<223> OTHER INFORMATION: His or Arg
<220> FEATURE:
<221> NAME/KEY: MOD_RES
<222> LOCATION: (14)..(14)
<223> OTHER INFORMATION: His or Arg
<220> FEATURE:
<221> NAME/KEY: MOD_RES
<222> LOCATION: (21)..(22)
<223> OTHER INFORMATION: His or Arg
```

```
<220> FEATURE:
<221> NAME/KEY: MOD_RES
<222> LOCATION: (24)..(25)
<223> OTHER INFORMATION: His or Arg

<400> SEQUENCE: 11

Xaa Xaa Xaa Xaa Xaa Arg Phe Ser Phe Xaa Xaa Ser Phe Xaa Leu Ser
1               5                   10                  15

Gly Phe Ser Phe Xaa Xaa Asn Xaa Xaa
            20                  25

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Lys Lys Lys Lys Arg Phe Ser Phe Lys Lys Ser Phe Lys Leu Ser
1               5                   10                  15

Gly Phe Ser Phe Lys Lys Asn Lys Lys
            20                  25

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Lys Lys Lys Lys Arg Phe Ala Phe Lys Lys Ala Phe Lys Leu Ala
1               5                   10                  15

Gly Phe Ala Phe Lys Lys Asn Lys Lys
            20                  25

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (8)..(9)
<223> OTHER INFORMATION: Any basic amino acid
<220> FEATURE:
<221> NAME/KEY: MOD_RES
<222> LOCATION: (11)..(11)
<223> OTHER INFORMATION: Any hydrophobic amino acid
<220> FEATURE:
<221> NAME/KEY: MOD_RES
<222> LOCATION: (12)..(12)
<223> OTHER INFORMATION: Any basic amino acid
```

```
<220> FEATURE:
<223> OTHER INFORMATION: See specification as filed for detailed
      description of substitutions and preferred embodiments

<400> SEQUENCE: 14

Xaa Xaa Xaa Arg Xaa Ala Xaa Xaa Xaa Ala Xaa Xaa
1               5                   10

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid
<220> FEATURE:
<221> NAME/KEY: MOD_RES
<222> LOCATION: (24)..(25)
<223> OTHER INFORMATION: Any basic amino acid
<220> FEATURE:
<223> OTHER INFORMATION: See specification as filed for detailed
      description of substitutions and preferred embodiments

<400> SEQUENCE: 15

Xaa Xaa Xaa Xaa Xaa Arg Xaa Ala Xaa Xaa Xaa Ala Xaa Xaa Leu Ala
1               5                   10                  15

Gly Xaa Ala Xaa Xaa Xaa Asn Xaa Xaa
            20                  25

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

Lys Lys Lys Arg Phe Ala Phe Lys Lys Ala Phe Lys
1               5                   10

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid
<220> FEATURE:
<221> NAME/KEY: MOD_RES
<222> LOCATION: (5)..(5)
<223> OTHER INFORMATION: Any hydrophobic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (8)..(9)
<223> OTHER INFORMATION: Any basic amino acid
<220> FEATURE:
<221> NAME/KEY: MOD_RES

```
<222> LOCATION: (11)..(11)
<223> OTHER INFORMATION: Any hydrophobic amino acid
<220> FEATURE:
<221> NAME/KEY: MOD_RES
<222> LOCATION: (12)..(12)
<223> OTHER INFORMATION: Any basic amino acid
<220> FEATURE:
<223> OTHER INFORMATION: See specification as filed for detailed
      description of substitutions and preferred embodiments

<400> SEQUENCE: 24

Xaa Xaa Xaa Arg Xaa Ser Xaa Xaa Xaa Ser Xaa Xaa
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any basic amino acid
<220> FEATURE:
<221> NAME/KEY: MOD_RES
<222> LOCATION: (6)..(6)
<223> OTHER INFORMATION: Any hydrophobic amino acid
<220> FEATURE:
<221> NAME/KEY: MOD_RES
<222> LOCATION: (8)..(8)
<223> OTHER INFORMATION: Any hydrophobic amino acid
<220> FEATURE:
<221> NAME/KEY: MOD_RES
<222> LOCATION: (9)..(10)
<223> OTHER INFORMATION: Any basic amino acid
<220> FEATURE:
<221> NAME/KEY: MOD_RES
<222> LOCATION: (12)..(12)
<223> OTHER INFORMATION: Any hydrophobic amino acid
<220> FEATURE:
<221> NAME/KEY: MOD_RES
<222> LOCATION: (13)..(13)
<223> OTHER INFORMATION: Any basic amino acid
<220> FEATURE:
<223> OTHER INFORMATION: See specification as filed for detailed
      description of substitutions and preferred embodiments

<400> SEQUENCE: 25

Xaa Xaa Xaa Xaa Arg Xaa Ser Xaa Xaa Xaa Ser Xaa Xaa
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
```

<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<223> OTHER INFORMATION: See specification as filed for detailed
      description of substitutions and preferred embodiments

<400> SEQUENCE: 26

Xaa Xaa Xaa Xaa Xaa Arg Xaa Ser Xaa Xaa Xaa Ser Xaa Xaa
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<223> OTHER INFORMATION: See specification as filed for detailed
      description of substitutions and preferred embodiments

<400> SEQUENCE: 27

Xaa Xaa Xaa Xaa Xaa Arg Xaa Ser Xaa Xaa Xaa Ser Xaa Xaa Leu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid

```
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<223> OTHER INFORMATION: See specification as filed for detailed
      description of substitutions and preferred embodiments

<400> SEQUENCE: 28

Xaa Xaa Xaa Xaa Xaa Arg Xaa Ser Xaa Xaa Xaa Ser Xaa Xaa Leu Ser
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<223> OTHER INFORMATION: See specification as filed for detailed
      description of substitutions and preferred embodiments

<400> SEQUENCE: 29

Xaa Xaa Xaa Xaa Xaa Arg Xaa Ser Xaa Xaa Xaa Ser Xaa Xaa Leu Ser
1               5                   10                  15

Gly

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
```

```
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<223> OTHER INFORMATION: See specification as filed for detailed
      description of substitutions and preferred embodiments

<400> SEQUENCE: 30

Xaa Xaa Xaa Xaa Xaa Arg Xaa Ser Xaa Xaa Xaa Ser Xaa Xaa Leu Ser
1               5                   10                  15

Gly Xaa

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<223> OTHER INFORMATION: See specification as filed for detailed
      description of substitutions and preferred embodiments

<400> SEQUENCE: 31

Xaa Xaa Xaa Xaa Xaa Arg Xaa Ser Xaa Xaa Xaa Ser Xaa Xaa Leu Ser
1               5                   10                  15

Gly Xaa Ser
```

```
<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<223> OTHER INFORMATION: See specification as filed for detailed
      description of substitutions and preferred embodiments

<400> SEQUENCE: 32

Xaa Xaa Xaa Xaa Xaa Arg Xaa Ser Xaa Xaa Xaa Ser Xaa Xaa Leu Ser
1               5                   10                  15

Gly Xaa Ser Xaa
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
```

<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(21)
<223> OTHER INFORMATION: Any basic amino acid
<220> FEATURE:
<223> OTHER INFORMATION: See specification as filed for detailed
      description of substitutions and preferred embodiments

<400> SEQUENCE: 33

Xaa Xaa Xaa Xaa Xaa Arg Xaa Ser Xaa Xaa Xaa Ser Xaa Xaa Leu Ser
1               5                   10                  15

Gly Xaa Ser Xaa Xaa
            20

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid
<220> FEATURE:
<223> OTHER INFORMATION: See specification as filed for detailed
      description of substitutions and preferred embodiments

<400> SEQUENCE: 34

```
Xaa Xaa Xaa Xaa Xaa Arg Xaa Ser Xaa Xaa Ser Xaa Xaa Leu Ser
1               5                   10                  15

Gly Xaa Ser Xaa Xaa Xaa
            20
```

```
<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid
<220> FEATURE:
<223> OTHER INFORMATION: See specification as filed for detailed
      description of substitutions and preferred embodiments

<400> SEQUENCE: 35

Xaa Xaa Xaa Xaa Xaa Arg Xaa Ser Xaa Xaa Ser Xaa Xaa Leu Ser
1               5                   10                  15

Gly Xaa Ser Xaa Xaa Xaa Asn
            20
```

```
<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any basic amino acid
<220> FEATURE:
<221> NAME/KEY: MOD_RES
<222> LOCATION: (7)..(7)
<223> OTHER INFORMATION: Any hydrophobic amino acid
<220> FEATURE:
```

```
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any basic amino acid
<220> FEATURE:
<221> NAME/KEY: MOD_RES
<222> LOCATION: (13)..(13)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any basic amino acid
<220> FEATURE:
<221> NAME/KEY: MOD_RES
<222> LOCATION: (18)..(18)
<223> OTHER INFORMATION: Any hydrophobic amino acid
<220> FEATURE:
<221> NAME/KEY: MOD_RES
<222> LOCATION: (20)..(20)
<223> OTHER INFORMATION: Any hydrophobic amino acid
<220> FEATURE:
<221> NAME/KEY: MOD_RES
<222> LOCATION: (21)..(22)
<223> OTHER INFORMATION: Any basic amino acid
<220> FEATURE:
<221> NAME/KEY: MOD_RES
<222> LOCATION: (24)..(24)
<223> OTHER INFORMATION: Any basic amino acid
<220> FEATURE:
<223> OTHER INFORMATION: See specification as filed for detailed
      description of substitutions and preferred embodiments

<400> SEQUENCE: 36

Xaa Xaa Xaa Xaa Xaa Arg Xaa Ser Xaa Xaa Xaa Ser Xaa Xaa Leu Ser
1               5                   10                  15

Gly Xaa Ser Xaa Xaa Xaa Asn Xaa
            20

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Lys Lys Lys Lys Arg Phe Ser Phe Lys Lys Ser Phe Lys Leu Ser
1               5                   10                  15

Gly Phe Ser Phe Lys Lys Asn Lys Lys
            20                  25

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Lys Lys Lys Lys Arg Phe Asp Phe Lys Lys Asp Phe Lys Leu Asp
1               5                   10                  15

Gly Phe Asp Phe Lys Lys Asn Lys Lys
            20                  25

<210> SEQ ID NO 39
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any basic amino acid or not present
<220> FEATURE:
<221> NAME/KEY: MOD_RES
<222> LOCATION: (5)..(5)
<223> OTHER INFORMATION: Any hydrophobic amino acid or not present
<220> FEATURE:
<221> NAME/KEY: MOD_RES
<222> LOCATION: (6)..(6)
<223> OTHER INFORMATION: Ser, Ala, Pro or Gly
<220> FEATURE:
<221> NAME/KEY: MOD_RES
<222> LOCATION: (7)..(7)
<223> OTHER INFORMATION: Any hydrophobic amino acid or not present
<220> FEATURE:
<221> NAME/KEY: MOD_RES
<222> LOCATION: (8)..(9)
<223> OTHER INFORMATION: Any basic amino acid or not present
<220> FEATURE:
<221> NAME/KEY: MOD_RES
<222> LOCATION: (10)..(10)
<223> OTHER INFORMATION: Ser, Ala, Pro or Gly
<220> FEATURE:
<221> NAME/KEY: MOD_RES
<222> LOCATION: (11)..(11)
<223> OTHER INFORMATION: Any hydrophobic amino acid or not present
<220> FEATURE:
<221> NAME/KEY: MOD_RES
<222> LOCATION: (12)..(12)
<223> OTHER INFORMATION: Any basic amino acid or not present
<220> FEATURE:
<223> OTHER INFORMATION: See specification as filed for detailed
      description of substitutions and preferred embodiments

<400> SEQUENCE: 39

Xaa Xaa Xaa Arg Xaa Xaa Xaa Xaa Xaa Xaa Xaa Xaa
1               5                   10
```